(12) United States Patent
Rose et al.

(10) Patent No.: US 10,973,471 B2
(45) Date of Patent: Apr. 13, 2021

(54) INTEGRATED MEDICAL DEVICE AND HOME BASED SYSTEM TO MEASURE AND REPORT VITAL PATIENT PHYSIOLOGICAL DATA VIA TELEMEDICINE

(71) Applicant: MEDWAND SOLUTIONS, INC., Las Vegas, NV (US)

(72) Inventors: Robert Howard Rose, Trabuca Canyon, CA (US); M. Samir Qamar, Las Vegas, NV (US)

(73) Assignee: MEDWAND SOLUTIONS, INC., Las Vegas, NV (US)

( * ) Notice: Subject to any disclaimer, the term of this patent is extended or adjusted under 35 U.S.C. 154(b) by 288 days.

(21) Appl. No.: 15/914,053

(22) Filed: Mar. 7, 2018

(65) Prior Publication Data

US 2018/0192965 A1    Jul. 12, 2018

Related U.S. Application Data

(63) Continuation of application No. PCT/US2016/050794, filed on Sep. 8, 2016.
(Continued)

(51) Int. Cl.
*A61B 5/00* (2006.01)
*A61B 1/227* (2006.01)
(Continued)

(52) U.S. Cl.
CPC ............ *A61B 5/7465* (2013.01); *A61B 1/227* (2013.01); *A61B 5/0002* (2013.01);
(Continued)

(58) Field of Classification Search
CPC ....... A61B 5/7465; A61B 5/01; A61B 5/0002; A61B 5/743; A61B 5/0022; A61B 5/0404;
(Continued)

(56) References Cited

U.S. PATENT DOCUMENTS 7,346,174 B1    3/2008  Smith
2008/0221930 A1*  9/2008  Wekell ................... G16H 10/60
                                                    705/3

(Continued)

FOREIGN PATENT DOCUMENTS

WO    2015145424 A1    10/2015

OTHER PUBLICATIONS

"Medwand: Features" (Nov. 22, 2014), http://Medwand.com/features.html, pp. 2, 4-5, 10.

*Primary Examiner* — Gary Jackson
*Assistant Examiner* — Sebastian X Lukjan
(74) *Attorney, Agent, or Firm* — Jonathan Kidney; Intelink Law Group, P.C.

(57) ABSTRACT

An integrated home based system to measure and report vital patient physiological data via telemedicine is disclosed. The integrated medical device is a personal, affordable, portable medical monitor, providing multiple critical vital sign data for real-time face-to-face communication with qualified health care professionals, direct from the comfort of your home (or wherever you may be travelling), whenever you need it. It is also linked to a secure patient medical record so the patient and/or healthcare professional can collect, archive and track information and trends.

22 Claims, 18 Drawing Sheets

Related U.S. Application Data

(60) Provisional application No. 62/215,595, filed on Sep. 8, 2015.

(51) Int. Cl.

| | | |
|---|---|---|
| *A61B 7/04* | (2006.01) | |
| *A61B 5/0205* | (2006.01) | |
| *A61B 5/024* | (2006.01) | |
| *A61B 5/01* | (2006.01) | |
| *G16H 40/67* | (2018.01) | |
| *G16H 80/00* | (2018.01) | |
| *G16H 10/60* | (2018.01) | |
| *A61B 5/0404* | (2006.01) | |
| *A61B 5/1455* | (2006.01) | |

(52) U.S. Cl.
CPC .............. *A61B 5/0022* (2013.01); *A61B 5/01* (2013.01); *A61B 5/02055* (2013.01); *A61B 5/02433* (2013.01); *A61B 5/0404* (2013.01); *A61B 5/6826* (2013.01); *A61B 5/743* (2013.01); *A61B 5/7425* (2013.01); *A61B 7/04* (2013.01); *G16H 10/60* (2018.01); *G16H 40/67* (2018.01); *G16H 80/00* (2018.01); *A61B 5/14552* (2013.01)

(58) Field of Classification Search
CPC .............. A61B 5/7425; A61B 5/02055; A61B 5/02433; A61B 5/6826; A61B 1/227; A61B 7/04; A61B 5/14552; G16H 40/67; G16H 80/00; G16H 10/60
See application file for complete search history.

(56) References Cited

U.S. PATENT DOCUMENTS

| | | | |
|---|---|---|---|
| 2013/0211265 A1* | 8/2013 | Bedingham | G06F 19/3418 600/483 |
| 2015/0045629 A1* | 2/2015 | Azimi | A61B 5/1118 600/301 |
| 2015/0057926 A1 | 3/2015 | Raz et al. | |

\* cited by examiner

MedWand DoctorView

URL: medwand.com/doctorview/login.html — 1100

1110 →

MedWand Session #: MB00043579
Physician Name: Dr. S. Qamar

MedWand Session SN: MW001298
Physician ID: MP00145

Session Time: 00:33:17
Examination Date: August 09, 2015

Less

- spO2 Sensor Status: Good
- Otoscope Sensor Status: Good
- Bluetooth Status: No Device Connected
- ECG Sensor Status: Good

Patient Information

Patient Name: Judy Moody
Date of Birth: 01/20/1970
Sex: Female
Telephone: 817-934-2382

1120 →

Address: 1024 Global Way
City: Dallas
State: Texas
Email: judy@gmail.com

Less

| | | |
|---|---|---|
| Blood Type: O+ | Allergies: Aspirin | Disease: Asthma [V] |
| Insurance Co.: Obamacare | Ins. #: 432676911BC9 | Ins. Type: PPO |
| Emp. #: 817-123-0038 | Emp. #: 817-123-0038 | Emp. State: Texas |
| PP #: 702-123-9876 | PP Fax #: 702-123-9765 | Recent Surgeries: Calectomy [V] |

Age: 45
Medication: Atenolol [V]
Employer: Pepsi Co.
Primary Phys: Dr. Qamar

Fig. 11

INTEGRATED MEDICAL DEVICE AND HOME BASED SYSTEM TO MEASURE AND REPORT VITAL PATIENT PHYSIOLOGICAL DATA VIA TELEMEDICINE

CROSS-REFERENCE TO RELATED APPLICATION(S)

This application claims the benefit and priority of International Application no. PCT/US2016/050794, filed Sep. 8, 2016, claiming the benefit of U.S. Provisional Patent Application No. 62/215,595, filed Sep. 8, 2015, the contents of which are hereby incorporated by reference in their entirety.

FIELD

This invention is directed to telemedicine. More particularly, this invention is directed to a synergistic system of a software and hardware configuration using a "home-based" low-powered, mobile, medical diagnostic device(s) with integrated medical sensors, for providing effective telemedicine with a remote clinician.

BACKGROUND

While telemedicine is already a multi-billion dollar industry providing remote doctor-patient consultations, there is currently no inexpensive, integrated portable, "home-based" solution to connect a patient to a health care professional and relay fundamental physiological information in real time during the consultation. Neither is there a single product that can collect, record and archive this information as part of an addressable Patient Medical Record (PMR) that the patient can authorize the health care professional to monitor and analyze for trend anomalies, or access themselves independently.

Other "telemedicine" devices on the market today are simply single purpose or clumsily developed products, each with different support software (if any exists at all) and do not provide the tools necessary for a typical doctor-like consultation. The telemedicine industry does not have a unified, coherent system that is easy to use for home use (the term "home" is broadly interpreted herein to mean any non-hospital/clinic location, therefore, home could include school office, remote (non-hospital) site, etc.) by a patient that is able to collect and integrate data from different critical vital sign monitors and present it in real time for telemedicine sessions, or in a properly formatted record for later use.

Therefore, in view of the above, various systems and methods are described below that address the industry's deficiencies.

SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

Various embodiments provide an integrated device that is personal, easy-to-use, providing multiple critical vital sign data for real-time face-to-face communication with qualified health care professionals, direct from the comfort of a user's home (or another location different from locations of the qualified health care professionals), whenever the need arises, and with a set of security features that link the device to a secure patient medical record so the patient and/or healthcare professional can collect, archive and track information and trends.

In one aspect of an embodiment, a compact, integrated, portable, diagnostic, multi-sensor telemedicine device is provided, comprising: a hand-held integrated portable housing, comprising: a finger port disposed at a proximal end of the housing, containing a pulse oximeter sensor adapted to measure a heart rate pulse of the user; a thermometer sensor disposed at a distal end of the housing, adapted to measure a temperature of the user; a digital stethoscope condenser microphone sensor disposed at palm-facing end of the housing, adapted to capture sound signals of the user's heartbeat; an otoscope camera sensor and a light source, sharing the distal end of the housing with the thermometer sensor, adapted to capture at least one of a still image and video of a targeted region in a cavity of the user; a low power micro-controller unit (MCU), communicating directly or indirectly with the above sensors and forwarding an encrypted data from the sensors to an external Internet-connected or Cellular-connected communication device, via at least one of a wired and wireless connection, a status indicator disposed on an exterior of the housing, providing a status and/or condition of the sensors and/or examination, wherein the device is configured to be self-administering by a user.

In another aspect of an embodiment, the device above is provided, further comprising an ECG pickup adjacent the palm-facing end of the housing for registering ECG data from the user; and/or further comprising a computer with teleconferencing capability coupled to the telemedicine device and having at least one of an Internet connection and cellular connection; and/or further comprising a remote server receiving the encrypted sensor data from the computer; and/or further comprising a software program running on the teleconferencing computer, providing teleconferencing with a medical professional, wherein the encrypted sensor data is presented to the medical professional; and/or wherein the software program displays the user's sensor data comprising at least one of pulse information, SpO2 information, finger temperature, forehead temperature, stethoscope reading, and otoscope reading; and/or wherein the software program further displays glucose reading and blood pressure reading; and/or wherein the device includes at least one of Bluetooth, near field, and USB communication capability; and/or wherein the device's camera includes a focusing lens; and/or further comprising at least two led arrays, one of the arrays being infrared; and/or wherein the server operates as a HIPPA compliant cloud storage unit; and/or wherein the device is self-powered via an internal battery; and/or wherein power for the device is via a USB connection; and/or wherein the remote server has access to a database of Patient Medical Records; and/or wherein the remote server provides encrypted information from a database of Patient Medical Records and stored user sensor data to the medical professional; and/or wherein remote server initiates a mobile alert to the medical professional or to a second medical professional; and/or wherein the software program allows the medical professional to contact and share user data with a second medical professional; and/or wherein the software program allows the medical professional to contact a second medical professional to join in the teleconference.

In yet another aspect of an embodiment, a method for conducting a telemedicine examination is provided, comprising: inserting a finger of a user into a finger port of a hand-held integrated portable housing, the finger port disposed at a proximal end of the housing; detecting a pulse and SPO2 of the user via a pulse oximeter sensor disposed in the finger port; detecting a temperature of the user via a thermometer sensor disposed at a distal end of the housing, the thermometer sensor inserted into an ear, mouth, or nasal cavity of the user; detecting a sound of the user's heartbeat via a digital stethoscope condenser microphone sensor disposed at palm-facing end of the housing; capturing at least one of a still image and video of a targeted region in a cavity of the user via an otoscope camera sensor and a light source, sharing the distal end of the housing with the thermometer sensor; processing and encrypting information from the sensors via a low power micro-controller unit (MCU); forwarding the encrypted information from the sensors to an external Internet-connected or Cellular-connected communication device, via at least one of a wired and wireless connection; and providing a status of operation on an exterior of the housing, wherein the examination is self-administered by the user.

In another aspect of an embodiment, the method above is provided, further comprising, teleconferencing with a medical professional with the encrypted information from the sensors; and/or further comprising, forwarding the encrypted sensor information to a remote server, wherein the remote server further interfaces with the teleconference.

Other aspects of the invention are described in the below detailed description of the drawings.

BRIEF DESCRIPTION OF THE DRAWINGS

FIG. 11 is a web-portal snap shot of subsequent steps in a MedWand session.

DETAILED DESCRIPTION OF THE DRAWINGS

Figure 1:
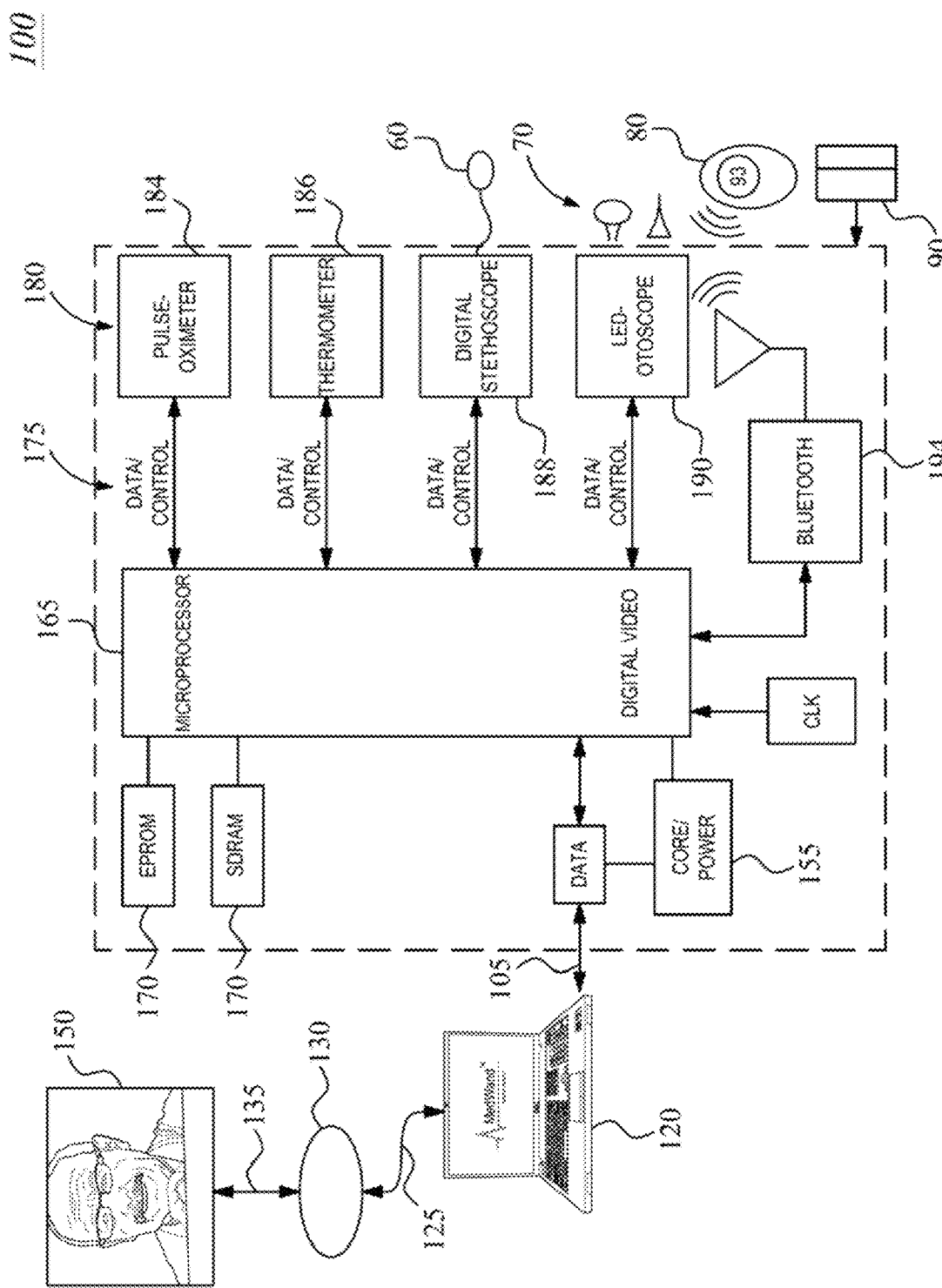
FIG. 1 is a functional diagram showing an operational layout of and exemplary MedWand system.

What is described herein is a novel integrated low-power diagnostic medical device, that is easy to self-administer for a patient, and includes a synergistic set of on-board medical tools, devices, and instruments to retrieve samples and forward medical diagnostic data to a first location of a medical professional and/or to analyze to a second location.

In various embodiments, a single integrated, user-operated, "handheld" sensored medical device (sometimes referred to as a MedWand device) provides the user of the device the ability to tap into a set of fundamental, vital signs measurement sensors integrated into the medical device. In some embodiments, the integrated sensored medical device or devices can be wired/wirelessly connected to a computing device, such as a PC, a laptop, a mobile communication device (such as a tablet or hand-held computer), and/or a mobile communications device, such as a smartphone. In some embodiments, one possible implementation of one or more of the integrated sensored medical device(s) is in the form of a wand about the size of a large electric toothbrush. The term "integrated" is understood to refer to an arrangement wherein the components/sensors of the medical device form a single unit, either constructed initially as a single unit or configured by the user to result in a single unit (that is, the user can "incorporate" other/optional sensors to the medical device to form a single operational unit). In some embodiments, the sensored medical device may comprise different non-integrated sensors, as will be apparent in the following descriptions and figures. In several embodiments, the integrated sensored medical device includes a pulse oximeter, an otoscope camera for ear examination (with attachments to allow views of the throat and nose), a contact thermometer, a digital stethoscope, and provision to support optional and third party devices such as glucose or blood pressure monitors. The data collected by these sensors can be aggregated into an encrypted file in the computing device which also presents an integrated gateway and crop application for the use (and medical professional at the other end) and sends to a secure Health Insurance Portability and Accountability Act of 1996 (HIPPA) compliant server for storage and access, both archive and real-time.

It should be appreciated that the embodiments described herein significantly differ from and improve upon currently existing options. For example, the integrated sensored medical device can be configured as a single, unified device with multiple vital sign sensors that formats and aggregates the collected data into a secure transmittable file for real time use by a teleconference connected health care professional and/or for archiving for later reference and analysis. The ability to have the primary sensors in a single unit allows data to be formatted into a single file and data/file transmission to be performed more securely and rapidly. While the prior art contemplates "remote" sensing of a patient's vital signs, etc., it is accomplished through separate individual devices, thereby making it impossible to transmit a complete package of the disparate data collected for each test to a connected healthcare professional or incorporate into a single database. Moreover, the use of multiple, separate independent devices adds to the complexity of use by the user, which further prevents successful operation thereof. For example, removing one medical device and attaching a second device and then removing that second device and attaching a third device is arguably a non-convenient (and thus, less usable) solution for any user. Thus, user error is a constant concern in the prior art.

In view of the above, as seen in some embodiments, by providing practically an "all-in-one," multi-sensor, personal medical device that is affordable, easy to use, with portable medical monitoring capability, while providing multiple critical vital sign data for real-time face-to-face communication with qualified health care professionals, is a significant paradigm shift in the telemedicine industry. Especially as it mitigates the need for office (doctor) visits which are difficult for remote-site patients as well as for handicapped, elderly patients. With digitization of the medical information, it is possible to link the data to a secure patient medical record, which the patient and/or healthcare professional can collect, archive and track information and trends. Further, information can be rapidly transmitted to other professionals for $3^{rd}$ party consultation. In this scenario, it is envisioned that one professional may perform a real-time examination using the MedWand system and upon examination of the "live" data, request a secondary professional to "log on" and review/manage the session with the user. The ability to timely add a second professional to the session, one who may ask the user to perform certain examination-specific follow on actions, for a more extensive evaluation, will reduce misdiagnoses and improve health treatment of users. In essence, routine or otherwise doctor visits can be preempted with an exemplary system. It is envisioned that medical stations having a MedWand system can be accessed at pharmacies, industrial nurse offices, schools, and even in homes, and so forth, if so desired.

It is understood that time density of measurements is a major benefit of the integrated sensored medical device of the present disclosure. For instance, normally a person may go to the doctor once or twice a year unless the person has a specific illness or emergency. Such infrequent doctor visits make it difficult to track the person's general health in significant levels of granularity. However, the integrated sensored medical device of the present disclosure allows for a resolution of data previously unknown in the field. If the person can get, for example, pulse, temp, Sp02, acoustic and camera images transmitted to a host server frequently (i.e., weekly) the doctor can plot trends for any or all of these parameters. Doing so provides a massive amount of context and will enable the doctor or healthcare professional to find clinical events that could not be detected in twice-yearly check-ups. The ability to "monitor" a patient with an ongoing condition, without visiting a clinic or hospital is considered the "Holy Grail" in the industry and is understood to be revolutionary in pre-post treatment protocols.

Also, usage of the integrated sensored medical device of some embodiments may produce continuous data accumulated over time, which can be very valuable for research purposes. In the case of medical data, the integrated sensored medical device can be used for many kinds of analysis including predictive medicine and monitoring of populations by geographic and/or demographic conditions. The integrated sensored medical device has the ability to collect this type of data and transfer it to computing devices that can execute deep statistical analysis, making the data itself very valuable. In this way, a person's routinely tracked vital readings (e.g., pulse, temp, Sp02, acoustic, and camera images, etc.) can be used to identify trends with respect to the person's past vital readings and can be used to compare the person's historical medical data against similar medical data from selected populations of other people. Similarly, the person's historically tracked vital readings can be compared to clinical models based on, for example, intra-system or extra-system populations.

The exemplary medical system may be comprised of various combinations of the following elements presented below. However, this list of possible constituent elements is not intended to limit the applicable elements. Persons having ordinary skill in the art relevant may understand there to be equivalent elements that may be substituted without changing the essential function or operation of the integrated medical system. Additionally, more or less elements may be utilized without departing from the spirit and scope of this disclosure.

1. Pulse Oximeter Sensor
2. Thermometer sensor (S2)
3. Digital Stethoscope Electret Condenser Microphone
4. Otoscope Camera
5. Bluetooth Receiver
6. Ultra Low Power MicroController/Processor
7. Clock circuit
8. Flash EPROM
9. SDRAM
10. USB Circuit
11. Computing Device Software
12. Secure, encrypted internet link
13. Cloud Server
14. Cloud Storage
15. Healthcare Provider Software
16. Integrated medical device Enclosure & Cables
17. Healthcare provider(s)' computing device
18. Computing Device Referring now to FIG. 1, which is a pictorial diagram 100 of typical hardware utilized in an exemplary MedWand system. The MedWand integrated device 110 is connected to an external computer/processor 120 (shown here, for example as a laptop) via a wired or wireless link 105. Direct external communication to the computer/laptop 120 can be being accomplished by a connected or wireless link 105, however, any other suitable communication interface/standard may be used. In some embodiments, where the MedWand integrated device 110 requires external power, link 105 may provide power, for example, through a wired USB connection or equivalent, etc. In some embodiments, the link 105 link may be Bluetooth or via wireless/cellular/etc. The computer/laptop 120 is connected via secondary link 125 (presumably, but not necessarily the patient's home internet gateway) to a Secure Cloud Server 130, which manages the information transfer to a physician 150 or other medical professional, via secure link 135. It should be appreciated that the links between the various hardware components may be physical links or wireless links, depending on implementation preference. Further, while a computer/laptop 120 can have abilities to directly connect to the Secure Cloud Server 130 (and bypass any intermediary router), any Internet-capable device can be used for channeling information forwarded by the MedWand device 110. For example, a smart phone, tablet, or other wireless device may be used. The computer/laptop 120 can also host the MedWand controlling software as well as facilitate communications with the medical professional, either thorough audio or video and audio. If hosting the controlling software, then the user may also be able to perform limited control of the MedWand device 110, such as initiating calibration, and other user-defined operations, according to design preference. One example would be to allow the user to authorize transmission of his/her medical data and/or session data to the medical professional or to another recipient 150 or to turn on/off a particular feature.

While the MedWand device 110 is an "all-in-one" purposed device, it can also communicate to other "medical" devices either directly integrated (e.g., physically coupled) or data coupled to the MedWand device 110, via separate device attachments, such as a stethoscope 60, lenses/Otoscope channel 70, Glucose Meter 80, Blood Pressure Cuff 90, etc. Some of these secondary medical devices/attachments can communicate with the MedWand device 110 via a direct or wireless connection, using the MedWand device's 110 external link 105 as the portal to the physician 150.

FIG. 1 also illustrates some of the hardware components "internal" to the MedWand device 110, which in some embodiments comprise an optional power source (e.g., battery) 155, Micro-Computing Unit (MCU) 165 or other equivalent processing hardware with associated memory (EPROM/SDRAM, etc.) 170 and control/data signals 175 to internal hardware/sensors 180 supporting functions such as a Pulse Oximeter 184, Thermometer 186, Stethoscope 188, Otoscope with LED 190, etc., in addition to external sensors, if so configured. Bluetooth 194 or other similar close-range wireless communication protocols are also enabled.

It should be appreciated that while FIG. 1 shows a given set of hardware for the internals of the Medwand device 110, other hardware components, different sensors, communication devices and so forth may be added/removed according to design preference. For example, future versions could include passive glucose monitoring as part of the pulse oximeter sensor set, and/or hemoglobin analysis. The MedWand device 110 could be expanded to include direct Internet connectivity (by passing data transfer through the computer/laptop 120), a more powerful processor, a display and direct user interface to eliminate the need for a host computing device 120. Further, a fall detector or some other sensor device could be implemented as options or re-configuration of the core unit.

Figure 2:
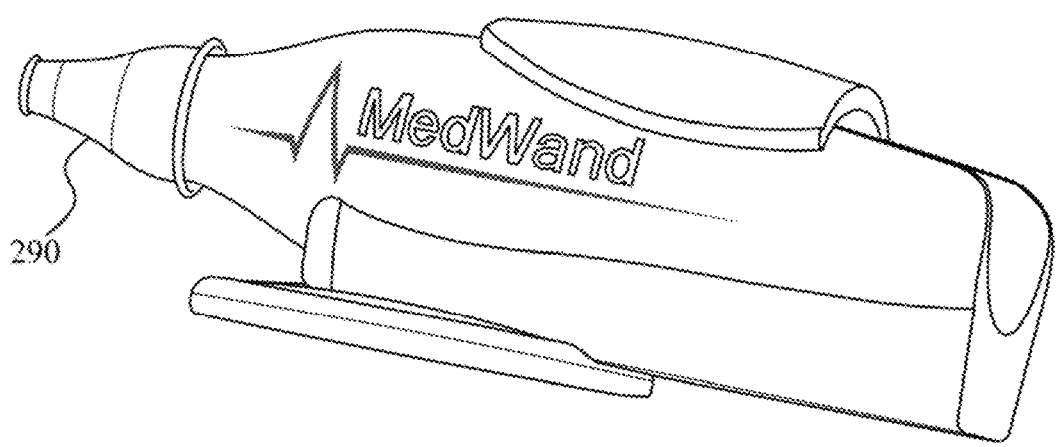
FIG. 2 is a side view of an exemplary MedWand user device.

FIG. 2 is a side view 200 of an exemplary MedWand device and show one possible design configuration, wherein the principal sensors are integrated into the device. Here, an Otoscope interface tip 290 is evident at the "front" of the device. As can be seen, this embodiment provides a single, multi-sensor system that is compact and easy to hold, allowing a non-medically trained person to perform a preliminary medical examination with relative ease.

Figure 3:
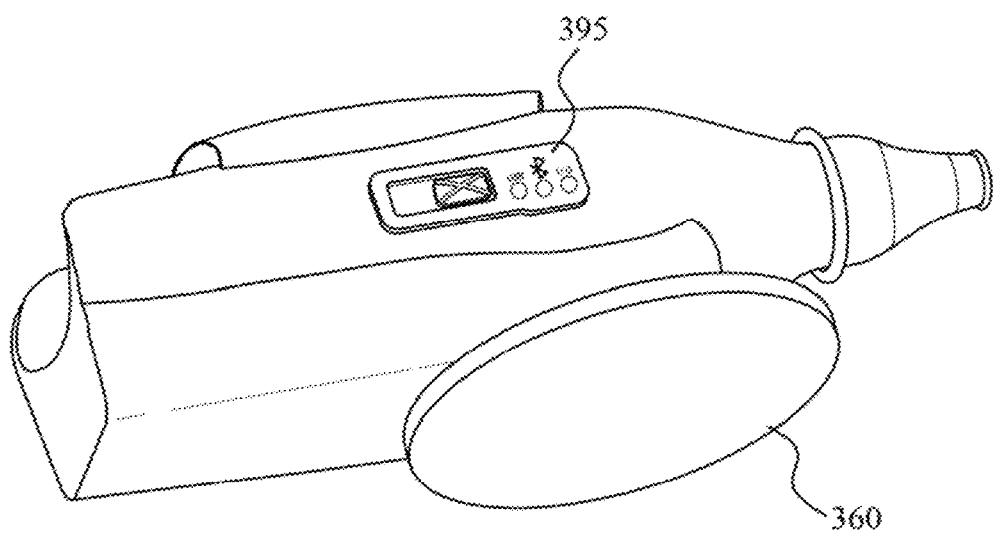
FIG. 3 is a bottom perspective view of an exemplary MedWand user device.

FIG. 3 is a bottom perspective view of the exemplary MedWand device of FIG. 2, showing the stethosocope face 360 and also status and power indicators 395.

Figure 4:
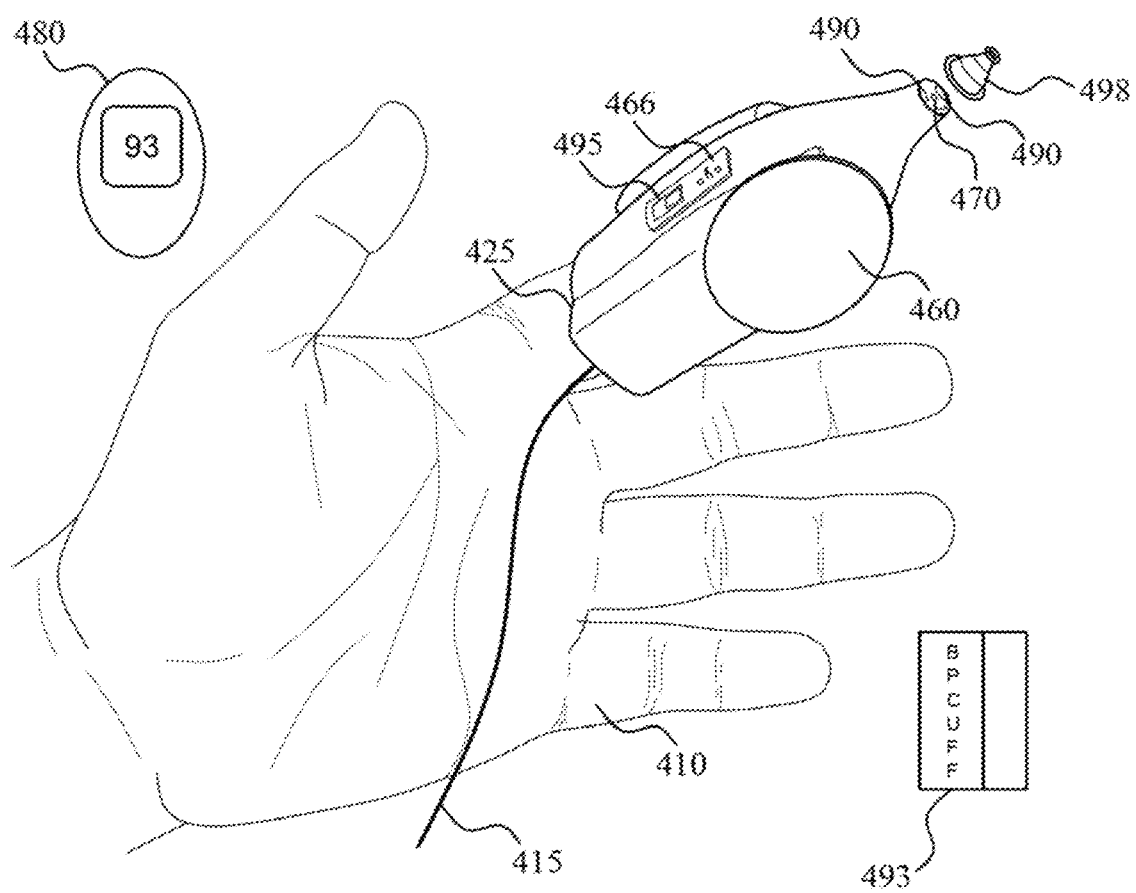
FIG. 4 is another view of the exemplary MedWand user device, in use by a user.

FIG. 4 is another view 400 of the exemplary MedWand device 110, in use by a user. Here, a finger of the user's hand 410 is inserted into the Pulse Oximeter's port 425. The Digital Stethoscope 460 is shown on the "bottom" of the MedWand device 110, but is understood to not be limited to the bottom. The "tip" of the MedWand device 110 is configured with a camera 470 and LED(s) 490 for Otoscope functions, shown here with an ear/nasal piece 498. A Thermopile (or similar) sensor and/or Thermometer (not shown) can also be facilitated to enable "in ear" temperature readings of the subject. Various power/communication cables 415, connection port 466 may be attached to the MedWand device 110. Status lights, displays, switches and associated controls 495 can be placed on a side of the MedWand device 110, for user feedback, etc. FIG. 4 also illustrates a separate Glucose Meter 480 and Blood Pressure Cuff 493 that is wireless capable, in communication with the MedWand device 110. It is evident from this Fig. that operation (from the user's perspective) is very easy and that most of the basic health indicator sensors are integrated into the MedWand device 110, with supplemental health sensors (480, 493, etc.) being in "communication" with the MedWand device 110.

FIGS. 1-4 illustrate a commercial embodiment of the MedWand device 110, with the respective elements/sensors shown at "particular" places on the device 110. However, it is understood that various elements/sensor locations may be altered, changed and the shapes of the elements/sensors may be also altered, changed according to design preference, without departing from the spirit and scope of this disclosure. Also, these Figs. show communication and power being supplied by a wired connection. In other embodiments, the communication may be transmitted wirelessly and power may arise from an internal power source, such as a battery.

Figure 5:
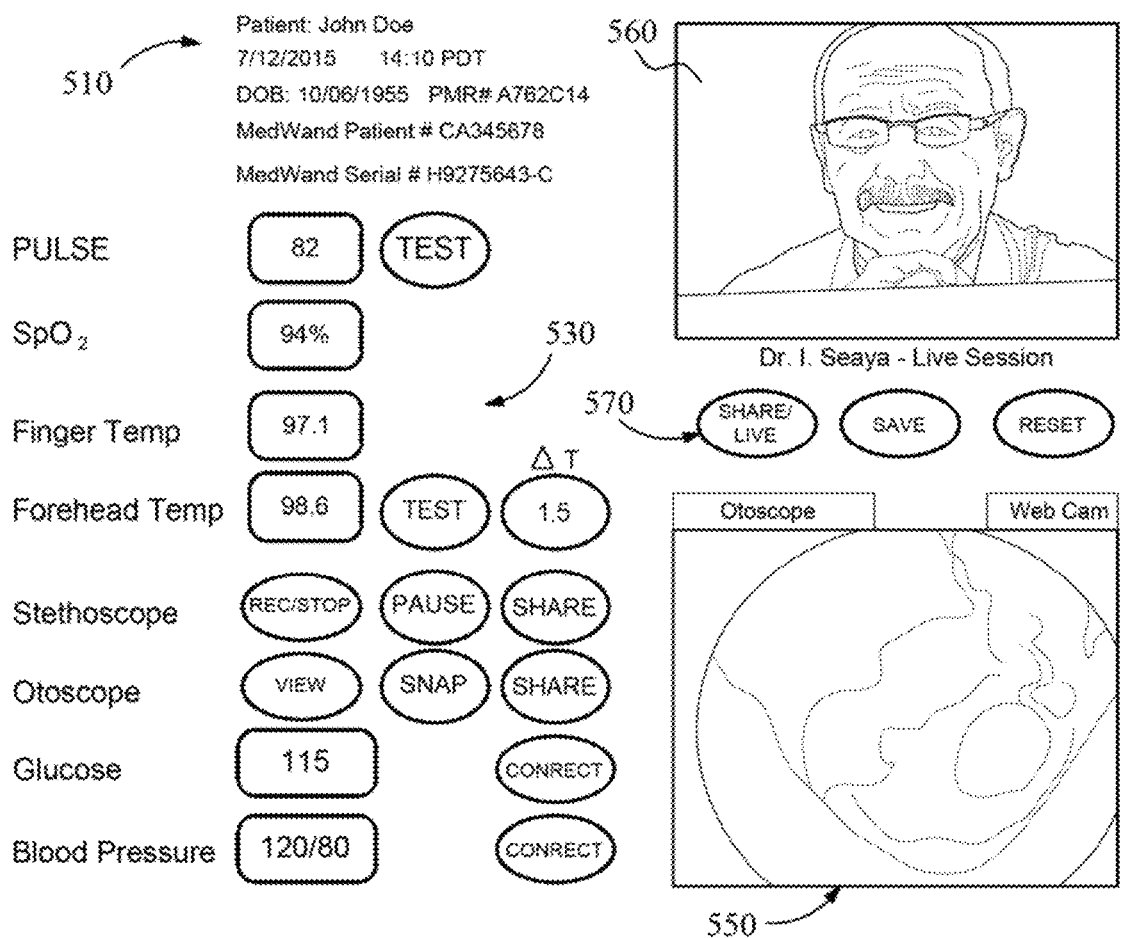
FIG. 5 is a sample illustration of one possible interface, showing the user's data to a professional.

FIG. 5 is an illustration 500 of the "back end" interface of the exemplary system wherein information from the MedWand device is presented to an examining professional. It is understood that sensor data for the examined person is forwarded from the MedWand device to a supporting server 130 (See FIG. 1) which then supplies a connection to the examining professional. In some embodiments, the laptop/computer 120 may have software that directly connects to the examining professional. The back end interface 500 contains patient and device information 510 with visual windows for any camera/image data 550 and the medical professional 560. In some embodiments, the medical professional image may be the user/patient (for example, from the medical professional's perspective). The individually sensed (real-time or aggregated) medical data 530 is displayed and various controlling options for the medical sensors are presented. Session options 570 are also presented. The interface provides a composite data window for the professional 560 to view and control the MedWand device, user's medical data, as well as communicate (via a computer/laptop) to the user.

In some instances, one or more of the medical data shown may be from a different examination or not originated from the MedWand device. As a non-limiting example, x-ray images may be added to the interface information to provide the professional 560 the user's x-ray information. FIG. 5 is demonstrative of the exemplary embodiment's ability to perform a live streaming examination with as needed information (e.g., x-ray) with a medical professional without anyone but the patient performing the instrument/sensor application. The breath of medical information that can easily obtained from the MedWand device is significant, and the ability to integrate this information with an examining medical professional is believed to be a significant shift in the industry paradigm. Further, with the ability to communicate with the patient, the medical professional can instruct the patient to perform additional examination activities (e.g., attach a separate detector, sensor, or deep breaths, etc.) while the patient is in the comfort of their own environment.

Evident in FIG. 5 is the suite of information available, for example, reference no. 530 shows medical data such as Pulse, SpO2, Finger Temp, Forehead Temp, Stethoscope, Otoscope, Glucose, Blood Pressure, image of ear or sinus 550, various sessions options 570, as well an image 560 (if so desired) of the medical professional. As discussed above, this information may be displayed on the medical professional's side, and/or some aspects of the information may be displayed on the user/patient's side. Also, while a laptop/computer may be the displaying platform, any suitable device that provides the necessary display, communication/ data capabilities may be used. For example, a smart phone, tablet, PC, smart TV, and so forth.

Figure 6:
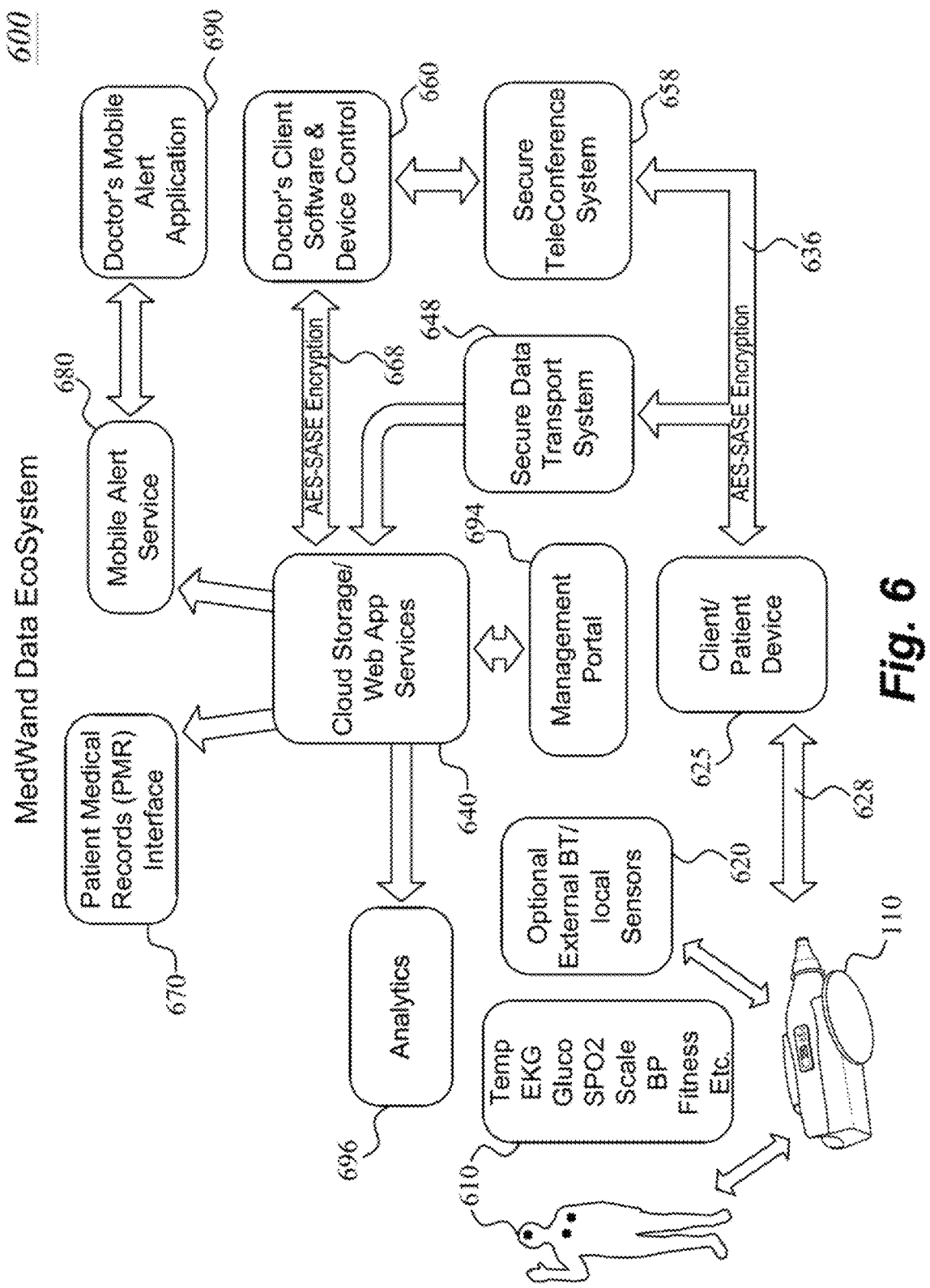
FIG. 6 is a simplistic block diagram showing various possible data paths in an embodiment of a MedWand system.

FIG. 6 is a block diagram 600 showing various Software and Hardware elements/modules and associated possible data paths in an embodiment of a MedWand system. Patient data 610 (and optional external devices 620) are procured by the MedWand device 110 and forwarded to the Client device 625 via a secure or encrypted link 628. The Client device 625 is "connected" to the system's Cloud 640 via a secure transport protocol 648 and also "connected" to a medical professional (shown here as a doctor) via a secure teleconferencing protocol 658. The system's Cloud 640 contains or manages the application services and also provides storage, as needed. Information from the system's Cloud 640 is also securely connected 668 to the Doctor's application 660, which is running on the Doctor's device (not shown) or via a web-portal to the system's Cloud 640 service supporting the application 660.

System Cloud 640 also has access, if so configured, to Patient Medical Records 670 and to Mobile Alert Services 680, which sends an alert to a Doctor's application 690, informing the Doctor of an emergency or request to join a session, and so forth. These latter connections may or may not be secure, depending on implementation preference. However, if patient information or other proprietary information is forwarded, secure protocols may be invoked. System Cloud 640 also has aspects of a Management Portal 694 and Analytics engine 696, for maintenance, management, etc.

It should be noted that individual patent data from and to the system's Cloud 640 may be transferred to a provider PMR 670 with patient and/or Doctor approval. It should also be noted that data accumulated across large demographic and/or geographic populations is understood to be valuable for predictive and preventive medicine. In some embodiments, the Analytics engine 696 may use this information, with de-personalization performed (to comply with privacy concerns, etc.) to obtain the predictive/preventive information.

Evident in FIG. 6 is the encryption between the client/patient portal device and the cloud storage and teleconference system, as well as between the cloud storage and the doctor-controlled MedWand device and/or doctor-used software. The "doctor" reviewing the MedWand data can decide what data is appropriate to retain and/or send to cloud storage. In some instances, mobile alert features may be triggered, for example, a senior doctor may be alerted to a threshold condition sensed by the MedWand device during an examination by another doctor or clinician. Or the result of a self-initiated examination can trigger an alert to a physician.

Figure 7:
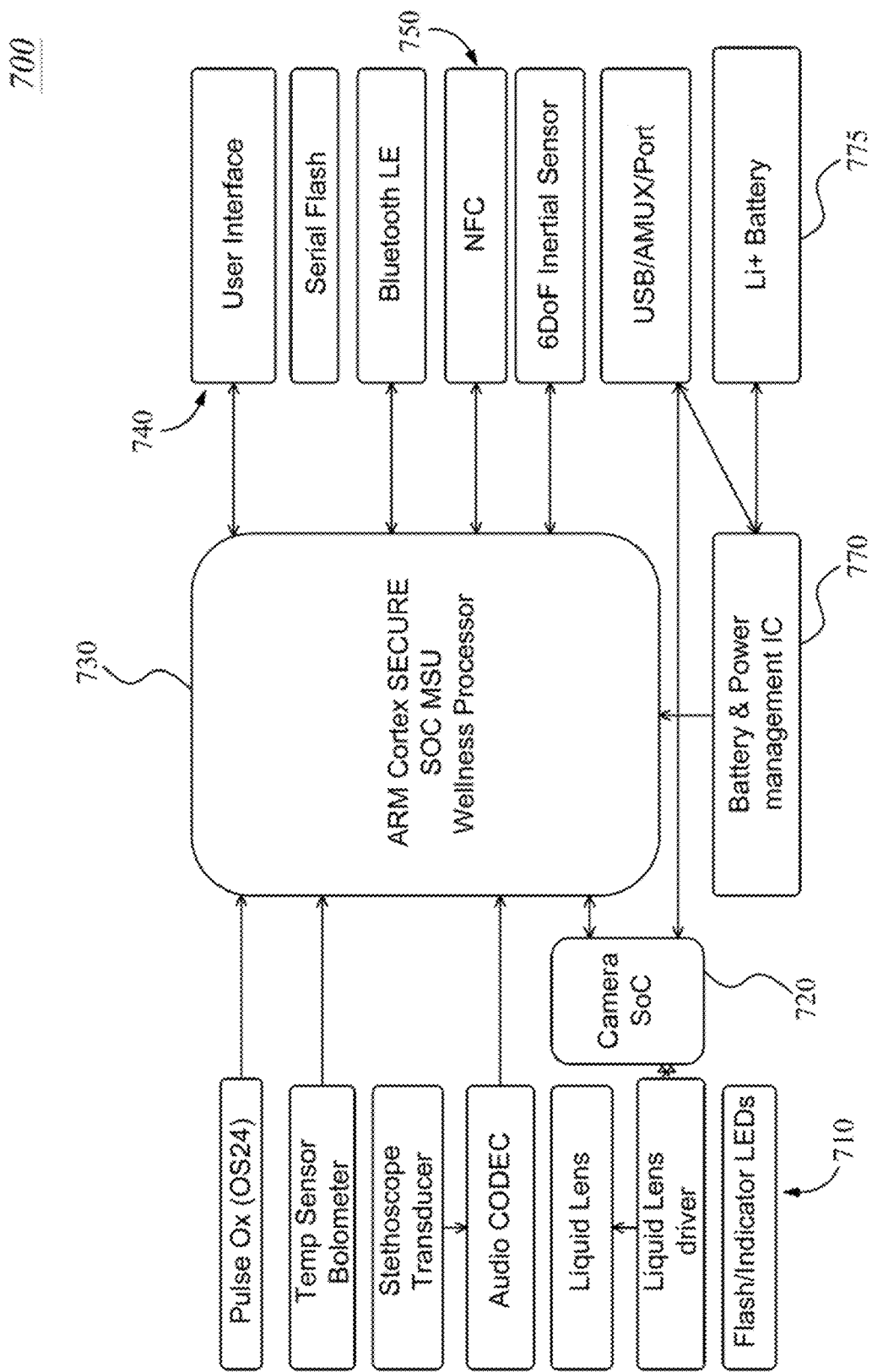
FIG. 7 is a block diagram illustrating the various medical hardware, computer hardware, and communication hardware that can be implemented in an embodiment of a MedWand user device.

FIG. 7 is a functional block diagram 700 illustrating the various medical hardware, computer hardware, and communication hardware that can be implemented in an embodiment of a MedWand user device. In an embodiment developed for commercial use, an ARM Cortex Wellness SOC processor 730 is used to host and manage the associated sensors/indicators 710 and communications 750. Various integrated sensors (Pulse Ox, Temp, Bolometer, Stethoscope, Audio, Inertial, Camera, etc.) are "hard wired" to the processor's data/communication interface. Camera 720 is contemplated for focus/autofocusing of images. Battery 775 and/or power module 770 supports the processor 730 and any sensors 730 and communications and/or memory hardware 740, as necessary. Processor 730 drives provides data/information to User Interface 740, which is supported on the user client hardware (not shown). Of importance, is the recognition that a "single" device capable of performing the medical test procedures typically found in a health check-up are integrated into the MedWand device, and produced in a form factor that is easy to use by a patient.

Figure 8:
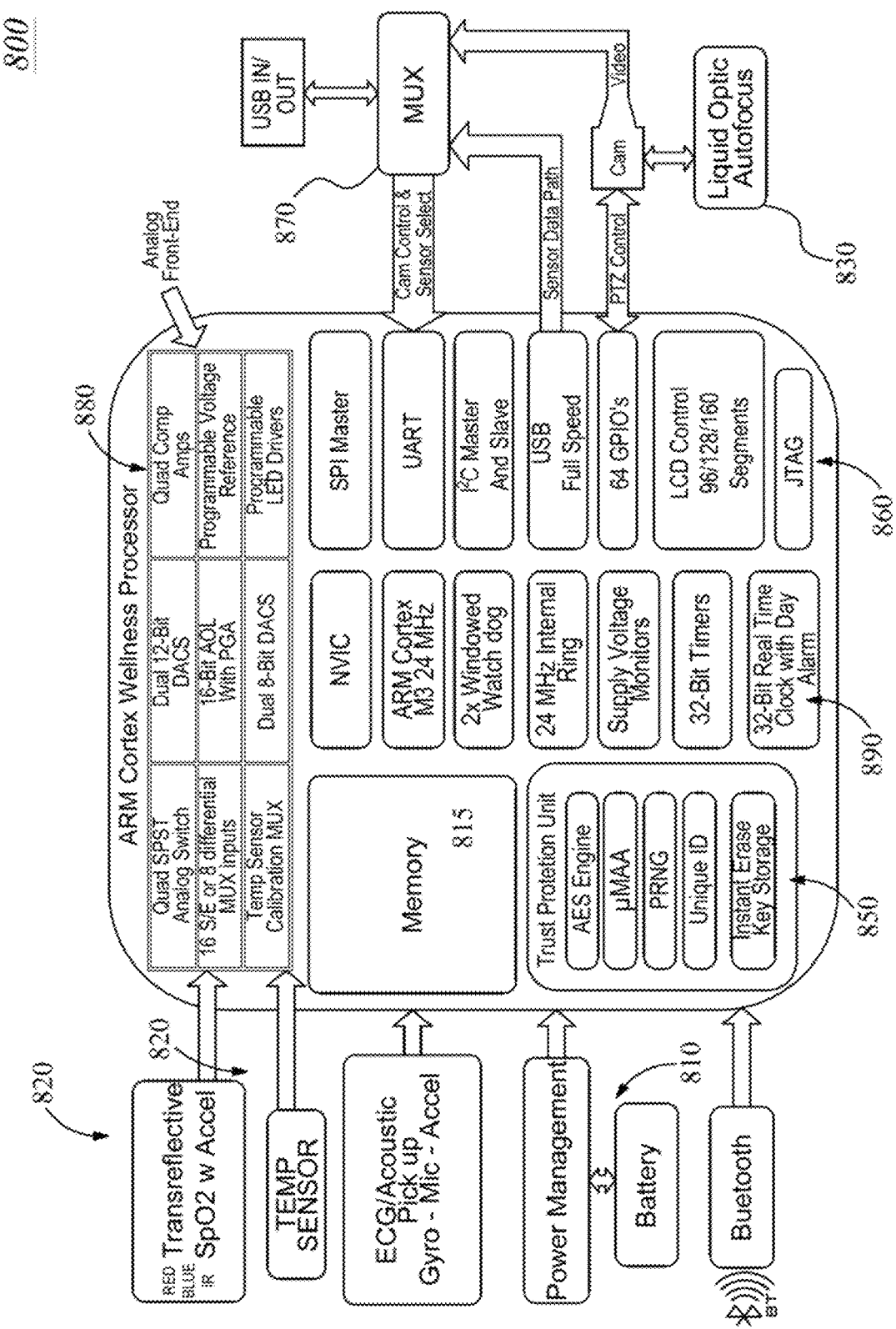
FIG. 8 is a block diagram illustrating internal hardware and software/module components in an embodiment of a MedWand user device.

FIG. 8 is a block diagram 800 illustrating the various medical hardware, computer hardware, and communication hardware that can be implemented in an embodiment of a MedWand user device. In an embodiment developed for commercial use, an ARM Cortex Wellness processor 810 with memory 815 is used to host and manage the associated sensors 820 (Transreflective SpO2 with Accelerometer, Temperature Sensor, ECG, Acoustic Pickup, Gyroscope, Microphone, Accelerometer), 830 (Camera Liquid Optic Autofocus) and sensor communications 840 (BlueTooth). A "Trust Protection Engine" 850 is implemented to have hardware-based security for data being read/sent through the processor. In some embodiments, the "trust" engine 850 may be software based or various portions off-loaded to the user's teleconferencing computer. Analog and Digital interfaces 860 are provided o the processor 810. Multiplexer 870 is used to control video as well as any USB in/out data. Additional capabilities are found in the analog front end 880 and clocks/timers 890.

Figure 9:
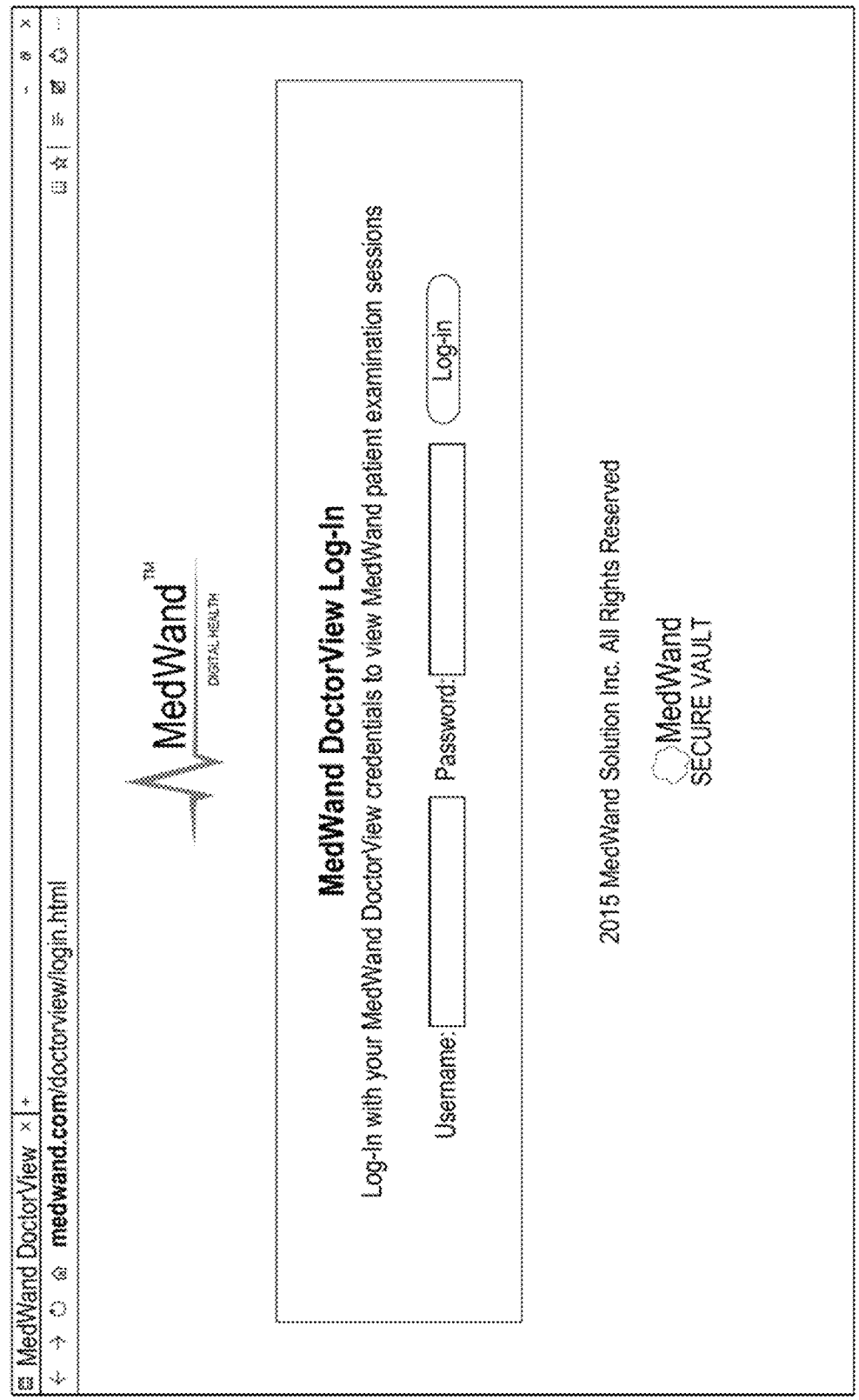
FIG. 9 is a web-portal snap shot of an initial MedWand session.

FIG. 9 is a web-portal snap shot 900 of an initial MedWand session, showing the MedWand Doctor's log-in procedure/prompting, and is understood to be self-explanatory. Commensurate log-in controls and security protocols, used in the log-in procedure are within the purview of one of ordinary skill in the art and therefore are not detailed herein.

Figure 10:
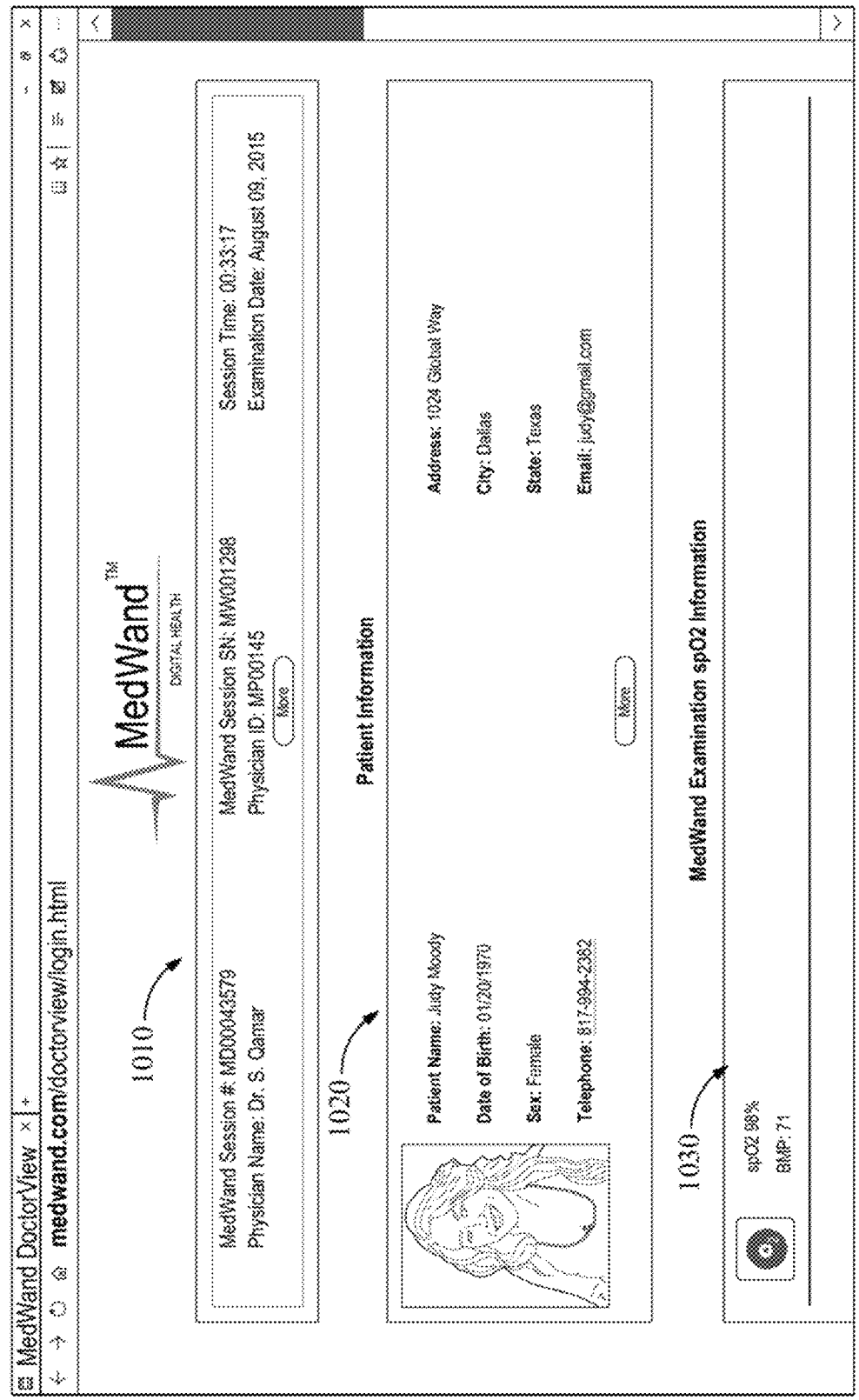
FIG. 10 is a web-portal snap shot of subsequent steps in a MedWand session.

FIG. 10 is a web-portal snap shot 1000 of subsequent steps in a MedWand session, showing the session information, physician name, MedWand device id and/or serial no., Physician ID, session time and date. Patient information 1020 such as name, birth date, sex, photo (if available), contact information is also presented. Various other information may be presented, to confirm the identity of the participants, equipment being used, etc., as needed. This Fig. shows the MedWand device's SpO2 information 1030 for the current patient. This information may be historical or real-time.

FIG. 11 is a web-portal snap shot 1100 of subsequent steps in a MedWand session, where it can be seen that a calibration or health/status 1110 of the MedWand device is presented. Further, additional medical history 1120 of the patient can be presented. In some instances, information of the patient's kin may be available, to determine if there is a hereditary trait that should be investigated.

Figure 12:
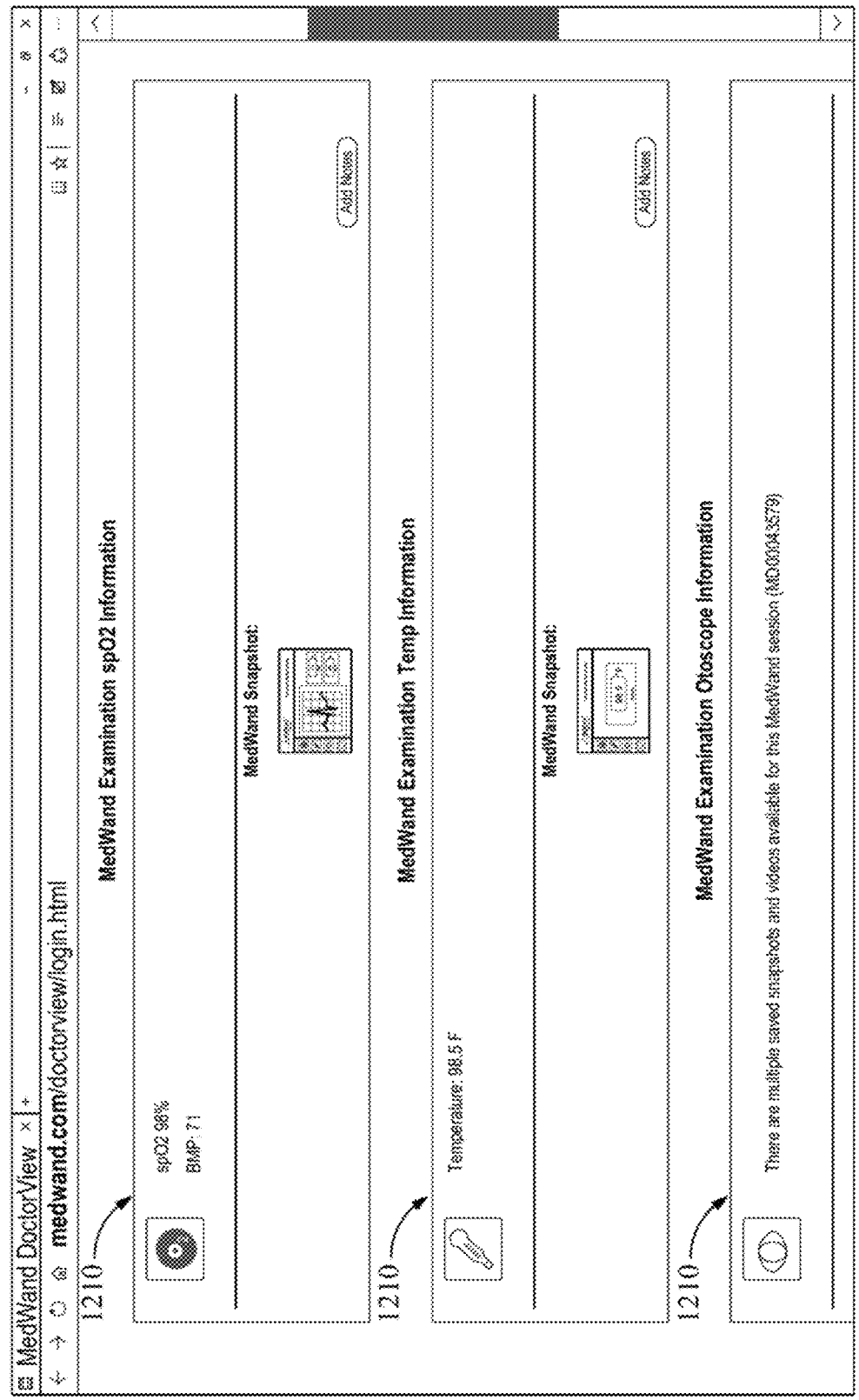
FIG. 12 is a web-portal snap shot of subsequent steps in a MedWand session.

FIG. 12 is a web-portal snap shot 1200 of subsequent steps in a MedWand session, showing additional MedWand sensor data 1210, such as the temperature of the patient and Otoscope.

Figure 13:
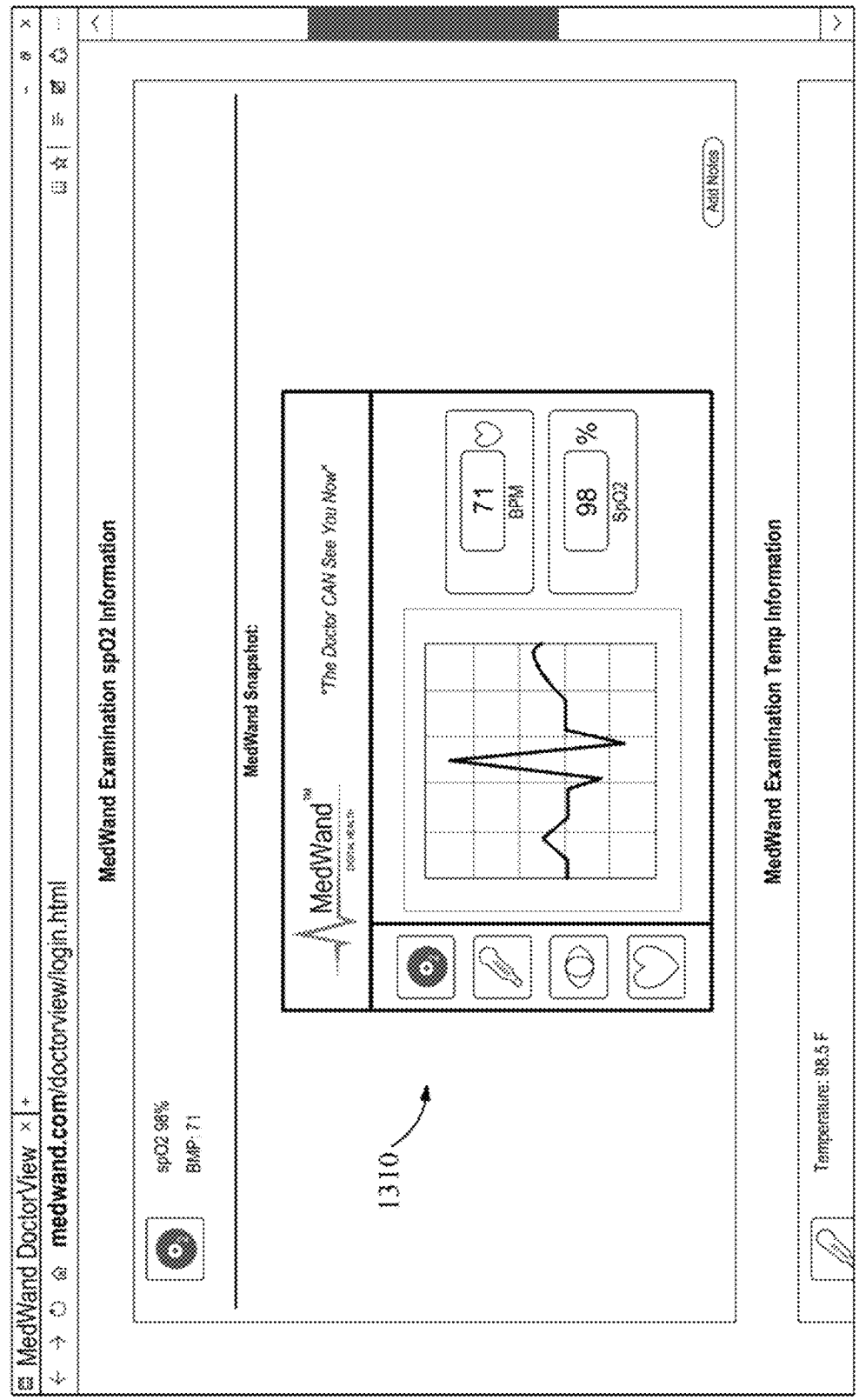
FIG. 13 is a web-portal snap shot of subsequent steps in a MedWand session.

FIG. 13 is a web-portal snap shot 1300 of subsequent steps in a MedWand session, showing the pulse rate and blood pressure 1310 in graphical form.

Figure 14:
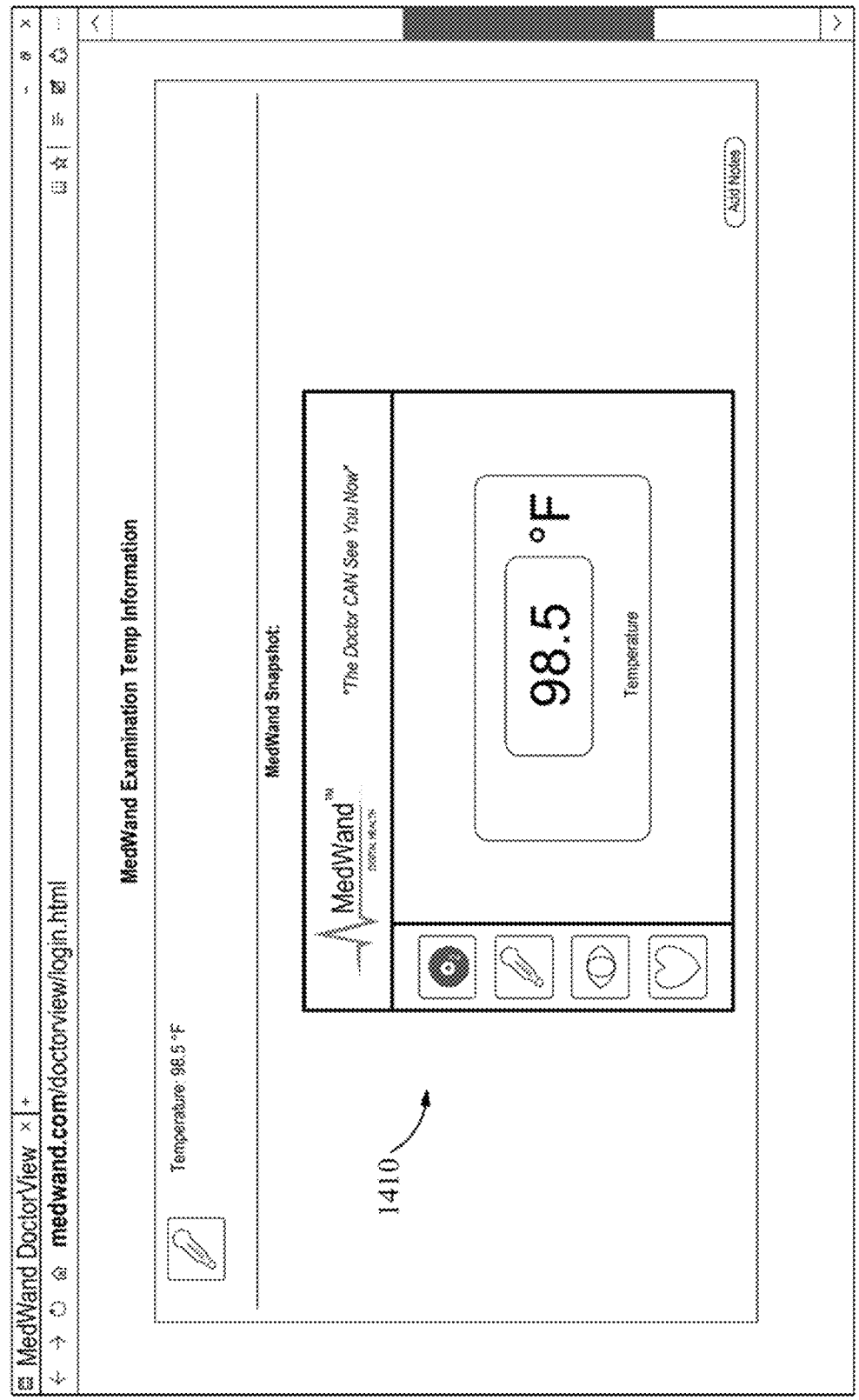
FIG. 14 is a web-portal snap shot of subsequent steps in a MedWand session.

FIG. 14 is a web-portal snap shot 1400 of subsequent steps in a MedWand session, showing the patient's temperature 1410.

Figure 15:
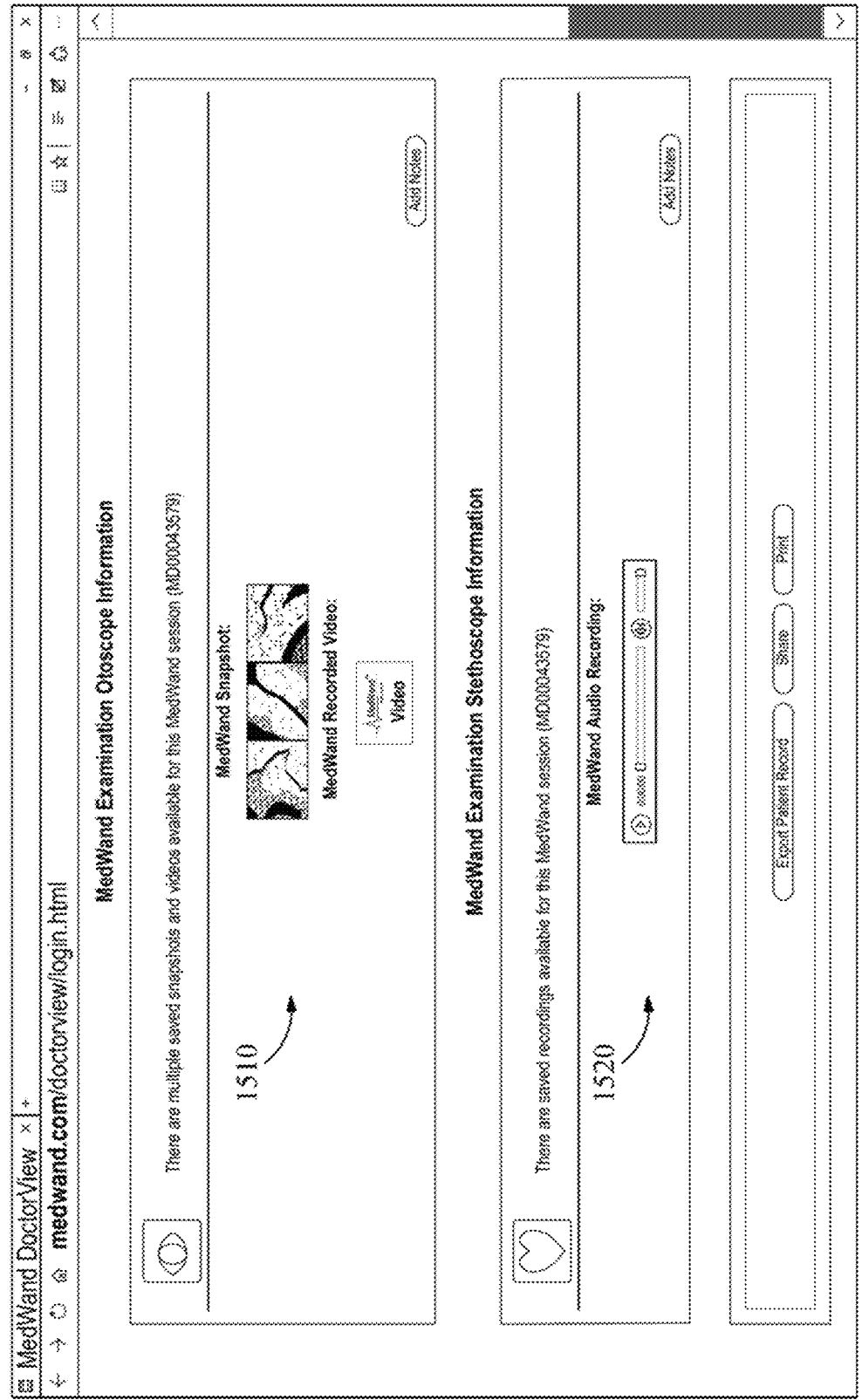
FIG. 15 is a web-portal snap shot of subsequent steps in a MedWand session.

FIG. 15 is a web-portal snap shot 1500 of subsequent steps in a MedWand session, showing Otoscope video 1510 and stethoscope audio file 1520.

As should be apparent from the above web-portal snap shots, the MedWand doctor/user interface is tailored to the MedWand device, and allows a homogenous platform for rapidly, concisely performing a telemedicine session, using the MedWand device as the primary medical sensor hardware. The ability for the doctor/professional to engage in real-time with the patient and "conduct" an examination via the user's simple manipulation of the MedWand device, having integrated sensors, and also examine the sensor data (live or historical) in a secure environment, is not seen in the prior art. The "ease" of use of such a configured system cannot be overstated.

With the above Figs. setting the stage, there are two contemplated scenarios under which a patient would use the exemplary integrated medical device and system. The first involves a real-time telemedicine session where the patient is connected via the Internet to a healthcare provider. The integrated medical device is connected to a computing device allowing a teleconference with the healthcare provider. In this case, while the teleconference is in progress with the remote healthcare provider, the integrated medical device facilitates real-time collection, sharing and transmission of various vital signs and information for the provider. With HIPPA compliant secure linkage to a secure teleconferencing service and patient medical record storage facility, the teleconference interface is built into the integrated medical device user software on the user's computing device. (in some instances, the software can be hosted on a server, being "displayed" on the user's computing device.)

When the patient invokes a telemedicine conference, he/she is connected in real-time to a healthcare provider (usually a doctor). The doctor would be running the healthcare provider's version of the integrated medical device software where he/she can see the integrated medical device data and also take control of the device to invoke tests and review data. Each vital parameter built into or passed through the integrated medical device can be selected from the user interface on the computing device. For example, either the doctor or the patient may want to measure the patient's pulse, SpO2, and finger temperature. The "Pulse" button/action is selected on the computing device. A help screen appears to guide the patient through proper usage or set-up for each test. When the test button is pushed or clicked on the user interface, a command is sent to the integrated medical device through (in some examples) the USB connection (or a wireless connection). Power for the integrated medical device can be supplied via a physical USB connection or via internal rechargeable battery depending on the version in use. Once the command is received by the USB interface, it is formatted and sent to the microprocessor (uP) in the device.

The second scenario would involve the patient collecting session data and sending it up to the records storage location for later analysis by a healthcare professional outside of a telemedicine session. The doctor can also set control parameters within the records storage application to monitor trends in the serial session data being sent by the patient, and be warned via electronic alarm to web enabled devices defined by the doctor if the data trends outside of configured parameters. While only two scenarios are described above, it is possible that additional scenarios of the MedWand system may be developed, therefore, the above examples should not be considered limiting, but be understood as presenting only the most obvious scenarios.

In some embodiments, the integrated medical device may limit usage of the on-board tools, devices, and/or instrumentation to a maximum number of tools that can be simultaneously used. For example, in some embodiments of the integrated medical device, only one sensor can be in use at any given time, so in this example the uP sends appropriate control signals over the IT bus to invoke a pulse Oximeter test. The data is returned to the uP where it is both stored in the session information in memory and sent back to the computing device via the USB connection (or wireless). Each sensor has a different function and some include audio and video, which can be recorded or taken as a snapshot (video still), but the workflow is essentially the same for each one except the Bluetooth devices, which may be connected to the integrated medical device first.

Multiple sensors may be invoked to derive secondary measurements of significant clinical value that cannot be derived from a single sensor. For example, the uP may invoke the pulse Oximeter and the digital stethoscope operating under the control of a single unified, highly accurate reference clock for the purpose of measuring. Thus, simultaneous measurements can be made, with an understanding that correlations between the measurements can be made.

For the integrated medical device to perform medical diagnostic operations, a process is performed composed of several steps, including (1) receiving command from host computing device to invoke a test, (2) determining which sensor to wake up, (3) sending appropriate control signals to the appropriate sensor to perform the test, (4) determining whether the sensor has sent data related to the test (i.e., waiting to receive data or has any data even been returned?) (5) after data is received, determine whether the data is within expected parameters (i.e., given the types of test, is the data in the expected range or readings?) (6) when the data is within expected range, continue to process step 10 without retesting, (7) when the data is not within expected, then loop to retest, (8) informing host of test failure, (9) testing again, (10) saving data in session buffer, and (11) sending data via output (e.g., USB) to computing device.

Practically speaking, the user may attach the integrated medical device to the host computing device and then invoke the integrated medical device software or application to begin testing. Testing may be done by following a set of on screen prompts. The patient, without any assistance, may be able to take Pulse, SpO2, finger temperature, record his/her heart& lung sound, take pictures of his/her ear, nose or throat, record glucose readings and take blood pressure all from a single integrated device accessed through a single easy to use user interface on a PC, laptop, tablet or smart phone. Other Bluetooth-enabled electronic devices (in addition to certain glucose and Blood Pressure units, like a scale for example) could be added and supported as well. All of the data is collected and presented in an easy to read single medical record that can appended to any PMR system. This data can be tracked, monitored and/or analyzed for trends or "out of control limit" readings. If connected to a health care profession during a real-time teleconference the patient can elect to share all of the vitals information as it is collected real-time simply by pressing the "share live" button on the interface. The doctor can also direct the patient for proper readings and even invoke some of the tests remotely. At the end of a session the patient or doctor merely needs to press the save button to store the data in a secure file on the host device, and also save it to a remote cloud PMR archive if that service is invoked in the patient profile.

It should be noted that due to security concerns, the information being "shared" on the respective display devices/platforms may simply be screen images and not actual data, per se. For example, through HIPPA compliant video conferencing system with screen share capabilities, the doctor will be able to engage in a two-way videoconference as well as observe all of the data reporting from the MedWand device. The doctor can actually be viewing the patients screen through the screen share function. The doctor is able to manipulate the MedWand device through the screen share interface that provides "remote control" capabilities of the patient's computing device/laptop, etc. During the exam however, no actual medical data is transferred across the Internet. What the doctor sees is a video representation of the data reporting. During the exam the doctor is able to "tag" and select certain data sets reported from the various sensors for recording and archiving in a remote record set in the patients computing device. At the end of the session the tagged data is compressed, encrypted, and sent to the data storage center in a separate, single, secure transmission.

Data from the several discrete sensors on or attached to the integrated medical device share a common control and data handling system. Data returned by the sensor is stored in user specific patient records. A session record is kept in memory on the device and test data is also sent to the host computing device for further consideration and actions via the communications data link. Session data is formatted to present a single, unified patient record of all vital signs, video and audio data collected during a given session. The host computing device formats and displays that data for use by the doctor and patient medical records archiving and analysis. In some versions of the integrated medical device all communication with the host device may be by Bluetooth only and power would be provided by an on board rechargeable battery.

In addition to patient vital sign/physical testing, diagnostic analysis can be performed. Algorithmic analysis, for example, can be performed to correlate one set of medical determinations with another. For instance, when the heart beats, the integrated medical device will pick up systole acoustically via the digital stethoscope on the device. The speed of sound in tissue is about 1500 m/s, so the device will pick it up in hundreds of microseconds. Then, using the pulse oximeter sensor, the device can see the systolic wave at the periphery (i.e., finger). Synchronous measurement of peripheral pulse (via the pulse oximeter) and cardiac acoustic signals (via the stethoscope) yields, at the very least, a phase delay between the two. This delay may by analyzed algorithmically to correlate with blood pressure, capillary dilation/contraction, arterial elasticity, fluid responsiveness, et al.

In addition to the phase delay described above, use of the integrated medical device allows for comparison of the character of a cardiac acoustic signal and the character of the plethysmographic wave at the periphery (pulse ox wiggle) to yield other markers of clinical significance. Further, cardiac acoustics and/or pulse ox can be further correlated with motion/flush in the camera image (otoscope and/or web cam on the host). The image dynamics (color, tone, motion etc.), correlated with the other sensors as described above will yield other data points of clinical significance.

Logistically speaking, if no Internet access is available where the patient is located, then the inventors have available an enterprise called MedWand Digital Health which offers the MedWand Global Clinic as a tool for remote connectivity. The MedWand Global Clinic connects a doctor to a patient anywhere on earth, even if it's a battlefield, a jungle, an oil rig, or any other remote place. Housed in a small ruggedized case that fits in the overhead space on an airplane, the Global Clinic has a MedWand device, a custom built super-ruggedized tablet, a built-in satellite phone, 4G station, Wi-Fi and even its own solar power system.

To accommodate various "payer" programs and scheduling, the doctor and patient profiles can be set in advance and driven (allowed to connect) by the various payer programs available throughout the system. This may include insurance coverage, direct primary care, pay per exam or many other possible doctor—patient relationships as defined by the particular healthcare value proposition in use. A session may be between a patient and his/her primary care physician, a telehealth service provider, or with any of an available pool of providers, depending on the program in use. To facilitate the session, the doctor or provider can log into an inventor-provided MedWand Telehealth Conference System to post available clinic hours. These hours can be posted and/or modified up to, for example, six months in advance.

Various examples of an actual implementation are presented. In one possible implementation, the patient logs into the same conference system with their unique patient ID and password to view available appointment times, and selects an appropriate appointment with the desired doctor or provider approved and pre-authorized by the system. Appointments may be scheduled, for example, two minutes to six months ahead in time. The patient will receive a reminder, for example, via both e-mail and text message in advance of the scheduled session. At appointment time (actually a predefined number of minutes before, as the patient appointment time and doctor availability are offset 5 (or other) minutes by the system to allow for patient log in and reduce doctor waiting time), the patient logs into the system and registers for the exam session via an interactive "virtual waiting room". The patient is prompted at this time to be sure their MedWand is connected and ready.

The doctor will see the patient in his/her virtual waiting room on the doctors PC, including all available information on the current reason for the visit and a link to the patient's medical history (if available). When the doctor is ready he/she will start the exam session with a single button selection.

The Exam

When the session begins, a two-way videoconference is established. The doctor will also see the status of the MedWand device and the sensor selection options within the application. The MedWand device also provides visual feedback of its status to the patient via an indicator, for example, amulti-colored LED array. The doctor can select any of the available sensors, in no required order.

Otoscope (Camera):

Located on the front of the MedWand device, the otoscope is a high definition camera with several attachment options (specula) that affix magnetically to the front of the device. The attachments are designed to aid in the viewing of various parts of the body including inside the ear, eyes, nose, throat and skin. The depth of focus can range from about 50 mm from the sensor plane to over 200 mm. Some of the attachments may contain additional lenses for enhanced viewing options. Camera pan, tilt and zoom are all controllable by the doctor through the video interface. Focus is automatic through a dynamic liquid lens system, or other equivalent.

Illumination is provided via an array of LED's located around the camera sensor, some which may be infrared capable. Therefore, dual or multiple illumination capabilities are contemplated using multiple arrays, the intensity being adjustable by the doctor for each array. Under infrared operation the otoscope can operate as an ophthalmoscope. The intensity (brightness) can be adjustable through a slider on the doctors' side of the application. At any time during the use of the otoscope/ophthalmoscope, the doctor can initiate a live video recording or take a snapshot of the content being viewed by the camera.

Stethoscope:

Located on the lower portion of the MedWand device, the stethoscope is a digital audio pick-up device that transmits a digitized audio signal to the MedWand processor. The audio stream is transferred real-time to the patient's computing device when selected as the active sensor. The doctor can monitor the stethoscope audio OR converse with the patient through a "push-to-talk" button on the doctors' interface that toggles the patient's audio input device selection from the MedWand device to the local computing device. At anytime the doctor can initiate an audio recording of the stethoscope pick-up. The doctor can select the duration of the recording or operate it manually. If no "stop" selection is made the sensor disconnects when another sensor is selected or the doctor returns to two-way voice communication with the patient.

Pulse Oximeter (SpO2):

There are two pulse oximeters on the MedWand device. Primary (SpO2-1) is located on the top of the MedWand device for use by inserting the forefinger into the pathway for a reading. The second unit (SpO2-2) is on the bottom of the MedWand device near the stethoscope pick up. Only the primary SpO2 sensor can be selected by the doctor in normal, single sensor operation mode. When a satisfactory reading is obtained the doctor can take a time stamped snapshot of the oxygen saturation and BPM data for inclusion into the exam data set.

IR Thermometer:

There is an Infrared thermometer located in the tip of the MedWand next to the camera sensor. It is designed for in-ear application and has a dedicated attachment for the front of the device to enhance its performance. Once a suitable reading is obtained the doctor can save it for inclusion into the exam data set.

ECG:

The MedWand device can contain a single/multiple channel, multiple lead (e.g., 2 lead) ECG system. Pickups can be on the bottom of each unit for each forefinger. There are two pickups on the lower part of the unit at either end of the stethoscope housing. The doctor can elect to start and stop an ECG recording at any time once proper contact is established. The duration can be set manually or predetermined in the doctor's application.

Bluetooth:

The MedWand device contains a Bluetooth radio and can be paired with any approved Bluetooth device. The profiles for approved devices, and their associated GUI's are loaded into both the patient and doctor applications. Therefor, when a Bluetooth device is paired with the MedWand device, it notifies the application which exact device is available. That device is then presented to the doctor as a sensor choice and will indicate for example: "Blood Pressure Cuff via Bluetooth". The doctor can then choose to save and data available from the remote device for inclusion into the exam data set.

Multi-Sensor Session

The MedWand device is designed to take simultaneous readings from multiple on-board sensors during a single placement on the body, usually the chest area above the heart. Specifically, the Stethoscope, ECG, the fingertip pulse oximeter and the chest pulse oximeter. This yields 12 possible correlation points that can be applied to advanced correlation algorithms. By correlating these readings in time and by other attributes such as amplitude and distortion, we can detect a multitude of medical states and conditions including fluid responsiveness, from which relative blood pressure can be derived. This is new territory. Some academic studies have been done on this subject and suggest that much deeper and meaningful diagnosis can be derived from correlated simultaneous sensor data.

Data Transmission

Once the exam concludes, the data the doctor selected for inclusion in the exam data set is formatted, compressed and encrypted into a single file. This file includes all of the preserved data reporting, and also all of the information pertinent to the exam including the patient profile and identifiers, doctor information, insurance claim information if appropriate, MedWand serial number and software revision, plus time, date and location stamps for the exam.

The data is automatically sent to the MedWand Digital Health cloud based secure data repository as an exam record for that patient by the patients computing device automatically in the background. The doctor is immediately notified that the exam data is available for review and notation through the MedWand application that includes the appropriate decryption and encryption tools. At his/her discretion the doctor can call the exam summary and make notations, both general and specific to each preserved observation. The record can be downloaded to the doctors PMR record or uploaded to a $3^{rd}$ party PMR record. MedWand's data repository presents the exam data file in a standard format that can be mapped into any PMR system if the system owner is provided with the data attributes and decryption tools from MedWand Digital Health.

Case Scenarios for MedWand

The following is a list of some possible conditions that MedWand device/system can be used to aid in diagnosis from a remote location. Note that most cases require more than one sensor. MedWand is understood to be the only device that consolidates all of these sensors into a single handheld device and then creates a consolidated medical record for the exam.

Diagnosis of Asthma Exacerbation/Acute Asthmatic Episode

MedWand Features Used:

SpO2

Respiratory Rate

Stethoscope

Diagnosis of Inner Ear Infection (Otitis Media)

MedWand Features Used:

Thermometer

Otoscope

Diagnosis of Outer Ear Infection (Otitis Externa)

MedWand Features Used:

Thermometer

Otoscope

Diagnosis of Seasonal Allergic Rhinitis

MedWand Features Used:

Otoscope (into nasal cavity)

Diagnosis of Conjunctivitis

MedWand Features Used:

Otoscope (over eye)

Diagnosis of Bronchitis

MedWand Features Used:

Stethoscope

Thermometer

Respiratory Rate

SpO2

Diagnosis of Pneumonia

MedWand Features Used:

Stethoscope

Thermometer

Respiratory Rate

SpO2

Heart Rate

Blood Pressure (via Bluetooth)

Initial Diagnosis of Congestive Heart Failure Exacerbation (subsequent confirmation required)

MedWand Features Used:
SpO2
Stethoscope
Respiratory Rate
EKG
Weight (via Bluetooth)
Initial Diagnosis of Acute Myocardial Infarction (subsequent confirmation required)
MedWand Features Used:
EKG
Heart Rate
Respiratory Rate
Initial Diagnosis of Septic Shock (subsequent confirmation required)
MedWand Features Used:
Temperature
Heart Rate
Blood Pressure (via Bluetooth)
Initial Diagnosis of Hypovolemic Shock (subsequent confirmation required)
MedWand Features Used:
Heart Rate
Blood Pressure (via Bluetooth)
Initial Diagnosis of Hyperglycemic/Diabetic Shock (subsequent confirmation required)
MedWand Features Used:
Glucose reading (via Bluetooth)
Blood Pressure (via Bluetooth)
Heart Rate
Respiratory Rate In a prototype version, the MedWand device was configured to have the ability to take multiple sensor readings simultaneously and report them as a unified data set, with the data corrected for processing and formatting time. Specifically, four sensors were monitored simultaneously and the time delays and characteristics (absolute values) between the occurrences of the sensor data were compared to indicate the fluid responsiveness of the human body as well as several other physiological dynamics. Coupled with other discrete readings such as body mass, even more correlated data can be accumulated and subjected to a diagnostic algorithm from which health metrics can be derived, including blood pressure (and many others). The four sensors in the prototype included:

EKG (minimum of 3 lead).
Acoustic occurrence of heart valve sounds at the outer chest wall (digital Stethoscope)
A Pulse Oximeter located at the fingertip detecting oxygen saturation and pulse.
A sensor located at the fingertip detecting heart rate and heart rate variance from which pulse transit time can be derived in conjunction with the ECG and stethoscope
Monitoring these and other potential sensors create multiple data points for correlation and subsequent analysis. A recent version of sensors utilizes a pulse oximeter that also measures heart rate variance and respiratory rate, therefore less independent sensors can be used as well as more sensors, depending on sensor type.

Figure 16:
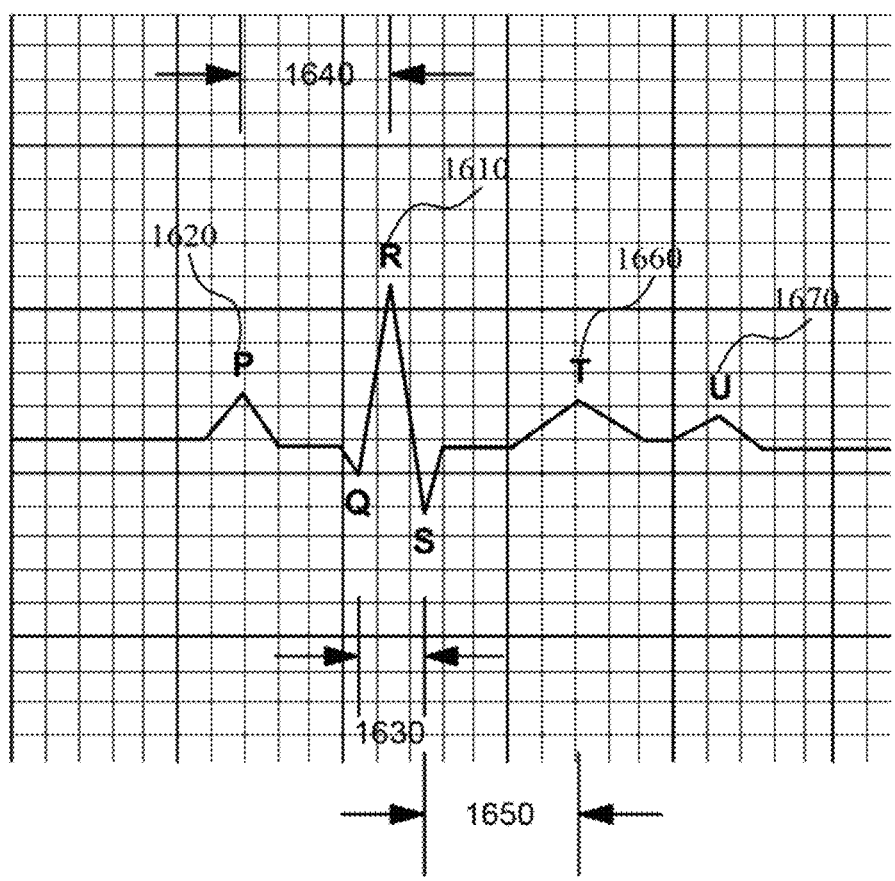
FIG. 16 is a plot of a representative EKG signal detected by the MedWand system.

FIG. 16 is a plot 1600 of a representative EKG signal detected by the MedWand system. It is understood that each stroke of a cardiac chamber creates a pressure wave that propagates/dissipates through the circulatory system and soft tissues. If we have a "starting gun" from the EKG signal at the beginning of a ventricular contraction, 'R', 1610 then we can look 'downstream' (at a number of different locations) at the PPG (photoplethysmograph) signal, as further described below. The marker P 1620 represents the atrial depolarization P-wave, QRS represents the period 1630 of depolarization of ventricles, PR segment 1640 represents the delay of AV node, ST segment 1650 represents the beginning of the ventricle repolarization, T 1660 the ventricular polarization, and U 1670 represents secondary activity.

Figure 17:
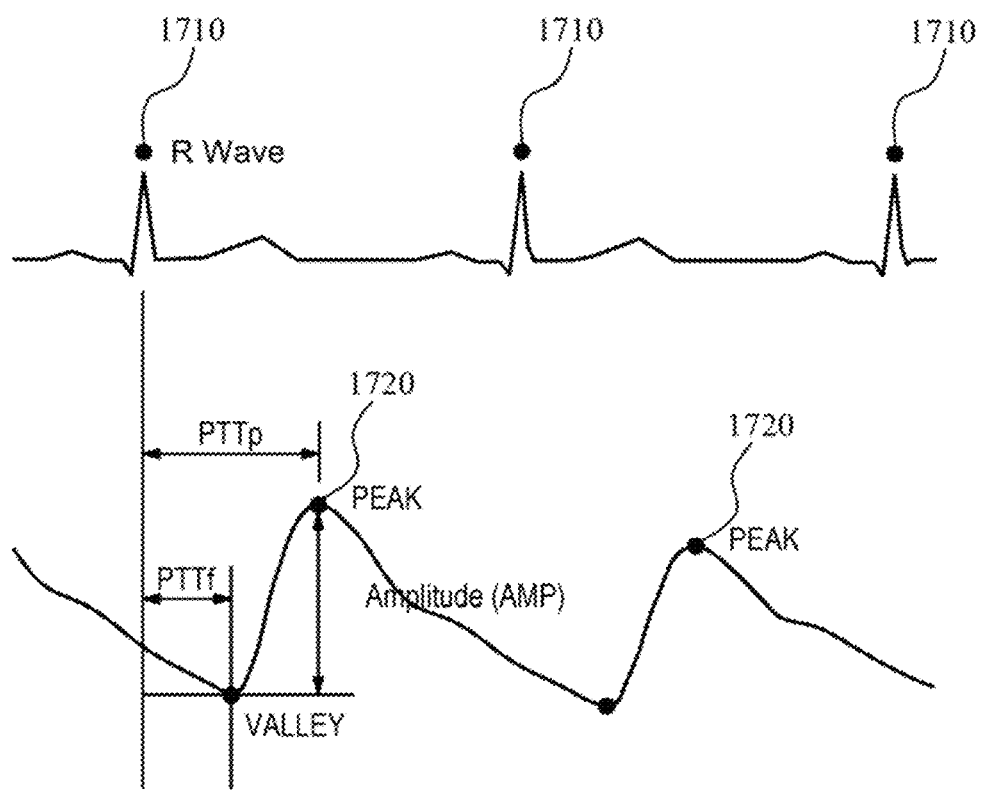
FIG. 17 is an analysis of a PPG signal detected by the MedWand System.

FIG. 17 is a description of a PPG signal 1700 detectable by the MedWand System. What the PPG signal indicates is that the first thing to look at is the delay between the Rwave 1710 and the systolic peak (marked just as 'PEAK' 1720 in this Fig.). The speed of sound in human tissues is very close to that of the speed of sound in water, about 1550 m/s. As blood is relatively incompressible—even while being full of soft tissue (erythrocytes) and dissolved gas—we would expect the speed of sound relationship to hold to first approximations. So, a meter worth of distance should be $1/1550$ worth of time=0.65 ms. Considering, per FIG. 17, that human heart rates can't go much higher than 4 Hz (240 bpm), the period between two peaks must be less than $1/4$=250 ms. As such, 'transmission time' in fluid is not a significant contributor to the delay between the Rwave and the systolic peak. Then what is causing the delay? It is believed to be a combination of Elasticity (tissue) and Damping (tissue and fluid shear loss).

If the tissues surrounding the CV had no elasticity, the heart would have to push harder, but blood flow would be instantaneous. With this elasticity, there is a delay, and a 'smoothing' of the input function from the ventricular contraction.

When the CV tissues, and the tissues surrounding them, stretch and relax, there is loss (visco-elastic damping) involved. As well, there is viscous loss in the bloodstream and between the bloodstream and the walls of the CV system. This is a function of wall area. As we get down to the capillary level, wall area goes way up. The overall heart/CV/tissue system can be seen as a mechanical driver attached to a mass/spring/damper system—at least a second-order system, to allow for the clear delay between the Rwave and the onset of pulsatile flow in the PPG.

Figure 18:
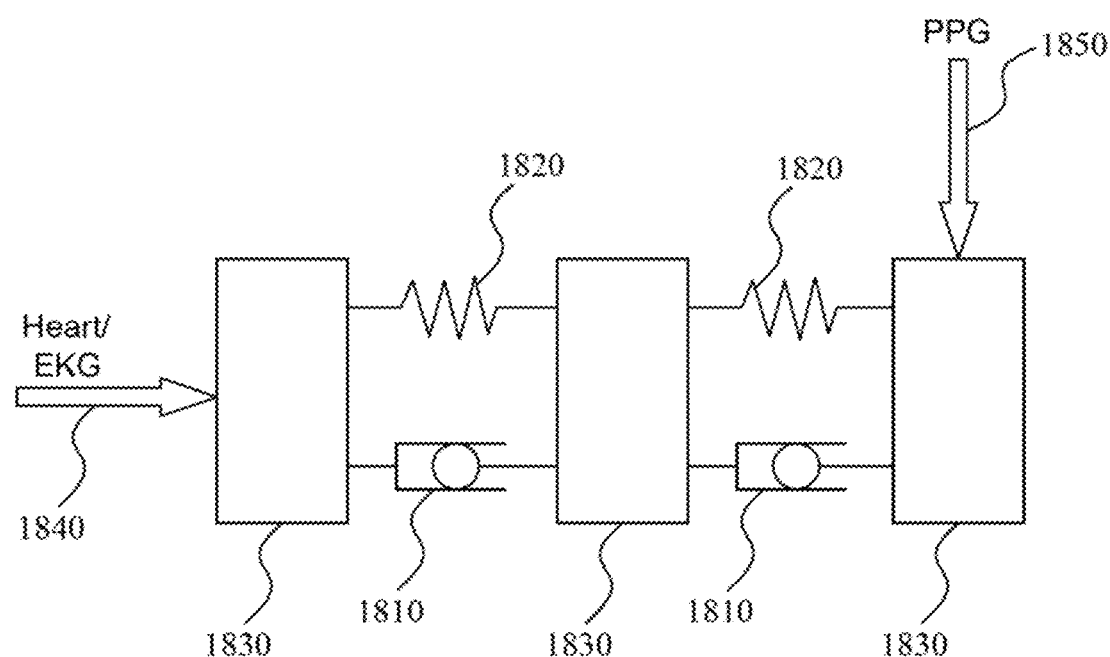
FIG. 18 is a diagram of a model of a heart, with respective mechanical equivalences.

FIG. 18 is a diagram 1800 of a theoretical model of a heart, with respective mechanical equivalences. For example, the CV/tissue system for a given unit length can be represented as an elastic series of dampeners 1810 with accompanying restorative springs 1820, between segments 1830 being operated on by the Heart and PPG. Models like this can be characterized with standard harmonic motion equations and coefficients—K1, K2 . . . G1, G2, . . . , etc. Deriving the coefficients from this model for a given EKG/PPG dataset could yield numerical matrices, which can be correlated with blood pressure.

Using the above information, we can apply a certain mechanical/mathematical model to the data, and derive a set of coefficients. Those sets of coefficients, for a given patient, may correlate with blood pressure. With additional demographic/health data, it may be possible to correlate a blood pressure number (in mmHg) to a given individual that is as accurate as cuff-based current practice. For example, it is believed that the exemplary system, with the heart modeling, the relative phase-delay between various distal locations could be used to detect asymmetries in the CV system or possible indications of arterial blockage. Aspects of the above analysis is referred to in the MedWand parlance as "Point to Point" Blood Pressure, or "Multi-Point Blood Pressure Analysis" or "BPsquared."

In some embodiments, one or more of the medical diagnostic tools, devices, or instruments of the integrated medical device could be reconfigured or adapted for use in veterinary medicine. Furthermore, continuous data accumulated over time can be very valuable for research purposes. In the case of medical data it can be used for many kinds of analysis including predictive medicine and monitoring of populations by geographic and/or demographic conditions. The integrated medical device has the ability to collect this type of data and transfer it to computing devices that can execute deep statistical analysis, making the data itself very valuable.

While the above-described embodiments have been described with reference to numerous specific details, one of ordinary skill in the art will recognize that modifications and changes can be made without departing from the spirit of this disclosure. Thus, one of ordinary skill in the art would understand that the invention is not to be limited by the foregoing illustrative details, but rather is to be defined by the appended claims.

What is claimed is:

1. A compact, integrated, portable, diagnostic, multi-sensor telemedicine device, comprising:
    a hand-held integrated portable housing, comprising:
        a finger port disposed at a proximal end of the housing, containing a pulse oximeter sensor adapted to measure at least one of an oxygen saturation, heart rate pulse, heart rate variance, and respiratory rate of the user, wherein the finger port is opposite a first set of sensors disposed at a distal end of the housing, enabling use of the first set of sensors by pointing of a finger placed in the finger port;
        a thermometer sensor disposed at an end of the housing, adapted to measure a temperature of the user;
        a digital stethoscope condenser microphone sensor disposed at a bottom, palm-facing side of the housing, between the ends of the housing, adapted to capture sound signals of at least the user's heartbeat and lungs;
        the first set of sensors, comprising a camera sensor and a light source, adapted to capture at least one of a still image and video of a targeted region in at least one of a cavity and body surface of the user;
        a low power micro-controller unit (MCU), communicating directly or indirectly with the above sensors and forwarding an encrypted data from the sensors to an external Internet-connected or Cellular-connected communication device, via at least one of a wired and wireless connection; and
        a status or display indicator disposed on an exterior of the housing, providing a status and/or condition of the sensors and/or examination,
    wherein the sensors are integrated with the housing and configured to take simultaneous reading from the finger port, the first set of sensors, the digital stethoscope, and the thermometer during a single placement on the body; wherein the entire multi-sensor telemedicine device is sized and configured to be positioned and used on a user's finger thereby allowing for self-administration by a user, and wherein a position of each sensor on the housing is configured to enable use of a desired sensor without changing an existing sensor configuration on the housing.

2. The telemedicine device of claim 1, further comprising an electrocardiogram (ECG) pickup adjacent the palm-facing side of the housing for registering ECG data from the user.

3. The telemedicine device of claim 1, further comprising, a computer with teleconferencing capability coupled to the telemedicine device and having at least one of an Internet connection and cellular connection.

4. The telemedicine device of claim 3, further comprising a remote server receiving the encrypted sensor data from the computer.

5. The telemedicine device of claim 4, further comprising a software program running on the teleconferencing computer, providing teleconferencing with a medical professional, wherein the encrypted sensor data is presented to the medical professional.

6. The telemedicine device of claim 5, wherein the software program displays the user's sensor data comprising at least one of pulse information, peripheral capillary oxygen saturation (SpO2) information, temperature, stethoscope reading, and otoscope reading.

7. The telemedicine device of claim 6, wherein the software program further displays glucose reading and blood pressure reading.

8. The telemedicine device of claim 1, wherein the device includes at least one of Bluetooth, near field, and universal serial bus (USB) communication capability.

9. The telemedicine device of claim 1, wherein the device's camera includes a focusing lens.

10. The telemedicine device of claim 1, further comprising at least two led arrays, one of the arrays being infrared.

11. The telemedicine device of claim 4, wherein the server operates as a Health Insurance Portability and Accountability Act (HIPPA) compliant cloud storage unit.

12. The telemedicine device of claim 1, wherein the device is self-powered via an internal battery.

13. The telemedicine device of claim 1, wherein power for the device is via a universal serial bus (USB) connection.

14. The telemedicine device of claim 4, wherein the remote server has access to a database of Patient Medical Records.

15. The telemedicine device of claim 4, wherein the remote server provides encrypted information from a database of Patient Medical Records and stored user sensor data to the medical professional.

16. The telemedicine device of claim 4, wherein remote server initiates a mobile alert to the medical professional or to a second medical professional.

17. The telemedicine device of claim 5, wherein the software program allows the medical professional to contact and share user data with a second medical professional.

18. The telemedicine device of claim 5, wherein the software program allows the medical professional to contact a second medical professional to join in the teleconference.

19. A method for conducting a telemedicine examination, comprising:
    inserting a finger of a user into a finger port of a hand-held integrated portable multi-sensor telemedicine device's housing, the finger port disposed at a proximal end of the housing and opposite a first set of sensors disposed at a distal end of the housing;
    detecting a pulse and peripheral capillary oxygen saturation (SpO2) of the user via a pulse oximeter sensor disposed in the finger port;
    detecting a temperature of the user via a thermometer sensor disposed at an end of the housing;
    detecting a sound of the user's heartbeat via a digital stethoscope condenser microphone sensor disposed at palm-facing side of the housing, between the ends of the housing;
    capturing at least one of a still image and video of a targeted region of the user via the first set of sensors comprising a camera sensor and a light source, by pointing the finger inserted in the finger port to move the first set of sensors to the targeted region;

wherein the sensors are integrated with the housing and configured to take simultaneous reading from the finger port, the first set of sensors, the digital stethoscope, and the thermometer during a single placement on the body;

processing and encrypting information from the sensors via a low power micro-controller unit (MCU);

forwarding the encrypted information from the sensors to an external Internet-connected or Cellular-connected communication device, via at least one of a wired and wireless connection; and providing a status of operation on an exterior of the housing, wherein the entire multi-sensor telemedicine device is sized and configured to be positioned and used on a user's finger thereby allowing the examination is able to be self-administered by the user and wherein use of a desired sensor can be made without changing an existing sensor configuration on the housing.

20. The method of claim 19, further comprising, at least one of teleconferencing with a medical professional with the encrypted information from the sensors, and forwarding the encrypted sensor information to a remote server, wherein the remote server further interfaces with the teleconference.

21. The telemedicine device of claim 1, wherein the camera and light source provide at least one of an otoscope, nasoscope, dermatoscope, laryngoscope and opthalmoscope capability.

22. The method of claim 19, wherein the capturing at least one of a still image and video of a targeted region of the user obtains at least one of otoscope, nasoscope, dermatoscope, laryngoscope and opthalmoscope information.

* * * * *